United States Patent [19]
Ring

[11] Patent Number: 5,849,877
[45] Date of Patent: Dec. 15, 1998

[54] ANTIGEN-BINDING SITES OF ANTIBODY MOLECULES SPECIFIC FOR CANCER ANTIGENS

[75] Inventor: David B. Ring, Palo Alto, Calif.

[73] Assignee: Chiron Corporation, Emeryville, Calif.

[21] Appl. No.: 483,199

[22] Filed: Jun. 7, 1995

Related U.S. Application Data

[63] Continuation-in-part of Ser. No. 323,566, Oct. 17, 1994, abandoned, which is a continuation of Ser. No. 141,375, Oct. 22, 1993, abandoned, which is a continuation of Ser. No. 605,399, Oct. 29, 1990, abandoned.

[51] Int. Cl.$^6$ ............................ C07K 16/00; C12N 5/00; C12N 15/00; C12P 21/04
[52] U.S. Cl. .................................. 530/387.1; 530/387.3; 530/387.7; 530/388.1; 530/388.2; 530/388.8; 435/69.7; 435/70.21; 435/172.1; 435/326
[58] Field of Search ........................... 530/387.1, 387.3, 530/387.7, 388.1, 388.2, 388.8; 435/69.7, 70.21, 172.1, 326

[56] References Cited

U.S. PATENT DOCUMENTS

| | | |
|---|---|---|
| 4,753,894 | 6/1988 | Frankel et al. . |
| 4,912,039 | 3/1990 | Riordan . |
| 4,938,948 | 7/1990 | Ring et al. . |
| 4,946,778 | 8/1990 | Ladner et al. . |
| 4,956,453 | 9/1990 | Bjorn et al. . |
| 5,091,513 | 2/1992 | Huston et al. . |
| 5,132,405 | 7/1992 | Huston et al. . |
| 5,206,352 | 4/1993 | Roninson et al. . |

FOREIGN PATENT DOCUMENTS

| | | |
|---|---|---|
| 2093866 | 10/1993 | Canada . |
| 0 174 810 A2 | 3/1986 | European Pat. Off. . |
| 0 519 596 A1 | 12/1992 | European Pat. Off. . |
| 2 276 169 | 9/1994 | United Kingdom . |
| WO 92/22653 | 12/1992 | WIPO . |

OTHER PUBLICATIONS

Huston et al., "Protein Engineering of Antibody Binding Sites: Recovery of Specific Activity in an Anti–digoxin Single–chain Fv Analogue Produced in *Escherichia coli*," *Proc. Natl. Acad. Sci.* (*USA*) (1988) 85:5879–5883.
Riechmann et al., "Reshaping Human Antibodies for Therapy," *Nature* (1988) 332:323–327.
Verhoeyen et al., "Reshaping Human Antibodies: Grafting an Antilysozyme Activity," *Science* (1988) 239:1534–1536.
Reeck et al, Cell, 1987, 50:667.
Lewin, Science, 1988, 237:1570.
Hmada et al, Cancer Res, 1990, 50: 3167–3171.
Padlan, Molecular Immunology, 1991, 28:489–498.

*Primary Examiner*—Lila Feisee
*Assistant Examiner*—Susan Ungar
*Attorney, Agent, or Firm*—Robinson & Associates; Paul B. Savereide; Robert P. Blackburn

[57] ABSTRACT

Novel compositions are provided that are derived from antigen-binding sites of immunoglobulins having affinity for cancer antigens. The compositions exhibit immunological binding properties of antibody molecules capable of binding specifically to a human tumor cell displaying a MDR phenotype. A number of synthetic molecules are provided that include CDR and FR regions derived from same or different immunoglobulin moieties. Also provided are single chain polypeptides wherein $V_H$ and $V_L$ domains are attached by a single polypeptide linker. The sFv molecules can include ancillary polypeptide moieties which can be bioactive, or which provide a site of attachment for other useful moieties. The compositions are useful in specific binding assays, affinity purification schemes, drug or toxin targeting, imaging, and genetic or immunological therapeutics for various cancers. The invention thus provides novel polypeptides, the DNAs encoding those polypeptides, expression cassettes comprising those DNAs, and methods of inducing the production of the polypeptides.

9 Claims, 2 Drawing Sheets

15D3 HC

```
  1  GAG GTG AAG GTT GTG GAG TCT GGG GGA GTC TTA GTG AGG CCT GGA
     E   V   K   V   V   E   S   G   G   V   L   V   R   P   G
     |---------------------------HFR1--------------------------

46  GGG TCC CTG AAA CTC TCC TGT GCA GCC TCT GGA TTC ACT TTC AGT
     G   S   L   K   L   S   C   A   A   S   G   F   T   F   S
     -----------------------------------------------------------|

91  AGG TAT ACC ATG TCT TGG GTT CGC CAG ACT CCG GAG AAG CGG CTG
     R   Y   T   M   S   W   V   R   Q   T   P   E   K   R   L
     |----HCDR1--------|  |-----------------HFR2-----------------

136  GAG TGG GTC GCA ACC ATT AGT AGT GGT GGT GGT AAC ACC TAC TAT
     E   W   V   A   T   I   S   S   G   G   G   N   T   Y   Y
     ---------------|  |---------------HCDR2--------------------

181  CCA GAC AGT GTG AAG GGT CGA TTC ACC GTC TCC AGA GAC AAT GCC
     P   D   S   V   K   G   R   F   T   V   S   R   D   N   A
     -----------------------|  |-------------------------------

226  ATG AGC AGC CTG TAC CTG CAA ATG AGC AGT CTG AGG TCT GAG GAC
     M   S   S   L   Y   L   Q   M   S   S   L   R   S   E   D
     ------------HRF3------------------------------------------

271  ACG GCC TTG TAT TAC TGT GCA AGA TAC GGG GCT GGT GAC GCC TGG
     T   A   L   Y   Y   C   A   R   Y   G   A   G   D   A   W
     -------------------------------|  |----------HCDR3---------

316  TTT GCT TAC TGG GGC CAA GGG ACT CTG GTC ACA GTT TCT GCA
     F   A   Y   W   G   Q   G   T   L   V   T   V   S   A
     ----------|  |--------------HFR4-------------------------|
```

```
  1  GAG CTC GCG ATG ACC CAG ACT CCA CTC TCC CTG CCT GTC AGT CTT
      E   L   A   M   T   Q   T   P   L   S   L   P   V   S   L
      |-----------------------------LFR1-----------------------------

46  GGA GAT CAA GCC TCC ATC TCT TGC AGA TCC AGT CAG AGC ATT GTG
      G   D   Q   A   S   I   S   C   R   S   S   Q   S   I   V
     ------------------------------|  |----------LCDR1-----------

91  CAT AGT ACT GGA AAC ACC TAT TTA GAG TGG TAC CTG CAG AAA CCA
      H   S   T   G   N   T   Y   L   E   W   Y   L   Q   K   P
     --------------------------------|  |-----------------------

136  GGC CAG TCT CCA AAG CTC CTG ATC TAC AAA GTT TCC AAC CGA TTT
      G   Q   S   P   K   L   L   I   Y   K   V   S   N   R   F
     -----------LFR2------------------|  |---------LCDR2---------

181  TCT GGG GTC CCA GAC AGG TTC AGT GGC AGT GGA TCA GGG ACA GAT
      S   G   V   P   D   R   F   S   G   S   G   S   G   T   D
     --|  |-----------------------------------------------------

226  TTC ACA CTC AAG ATC AGT AGA CTG GAG GCT GAG GAT CTG GGA GTT
      F   T   L   K   I   S   R   L   E   A   E   D   L   G   V
     ---------------LFR3-----------------------------------------

271  TAT TAC TGC TTT CAA GGT TCA CAT TTT CCT CGG ACG TTC GGT GGA
      Y   Y   C   F   Q   G   S   H   F   P   R   T   F   G   G
     -----------|  |-------------------LCDR3-----------|  |---------

316  GGC ACC AGG CTG GAA ATC AAG
      G   T   R   L   E   I   K
     ---------LFR4-------------|
```

FIG. 2

ANTIGEN-BINDING SITES OF ANTIBODY MOLECULES SPECIFIC FOR CANCER ANTIGENS

CROSS-REFERENCE TO RELATED APPLICATION

This application is a continuation-in-part of U.S. patent application Ser. No. 08/323,566, filed Oct. 17, 1994, now abandoned, which is a continuation of U.S. patent application Ser. No. 08/141,375, filed Oct. 22, 1993, now abandoned, which is a continuation of U.S. patent application Ser. No. 07/605,399, filed Oct. 29, 1990, which now abandoned, applications are incorporated by reference herein in their entireties and from which priority is claimed pursuant to 35 USC §120.

TECHNICAL FIELD

The present invention relates to novel compositions derived from antigen-binding sites of immunoglobulin molecules specific for cancer antigens. More particularly, the invention relates to molecules that are capable of exhibiting immunological binding properties of antibody antigen-binding sites, and which are useful in specific binding assays, affinity purification schemes, drug or toxin targeting, imaging, and genetic or immunological therapeutics for various cancers among other uses. The invention relates to novel polypeptides having structure and function substantially homologous to native antibody antigen-binding sites, the DNAs encoding those polypeptides, expression cassettes comprising those DNAs, and methods of inducing the production of the polypeptides.

BACKGROUND

Antibodies are normally synthesized by lymphoid cells derived from B lymphocytes of bone marrow. Lymphocytes derived from the same clone produce immunoglobulin of a single amino acid sequence. Lymphocytes cannot be directly cultured over long periods of time to produce substantial amounts of their specific antibody. However, Kohler et al. (1975) *Nature* 256:495–497, demonstrated that a process of somatic cell fusion, specifically between a lymphocyte and a myeloma cell, could yield hybrid cells which grow in culture and produce a specific antibody called a "monoclonal antibody" (hereinafter also referred to as "MAB"). The resulting hybrid cell was called a "hybridoma". A monoclonal antibody belongs to a group of antibodies whose population is substantially homogeneous, i.e. the individual molecules of the antibody population are identical except for naturally occurring mutations. Myeloma cells are lymphocyte tumor cells which, depending upon the cell strain, frequently produce an antibody themselves, although "nonproducing" strains are known.

The development of monoclonal antibody technology has provided an enormous opportunity for science and medicine in implementing research, diagnosis and therapy. Monoclonal antibodies are used in radioimmunoassays, enzyme-linked immunosorbent assays, immunocytopathology, and flow cytometry for in vitro diagnosis, and in vivo for diagnosis and immunotherapy of human disease. Waldmann, T. A. (1991) *Science* 252:1657–1662. In particular, monoclonal antibodies have been widely applied to the diagnosis and therapy of cancer, wherein it is desirable to target malignant lesions while avoiding normal tissue. See, e.g., U.S. Pat. Nos. 4,753,894 to Frankel, et al.; 4,938,948 to Ring et al.; and 4,956,453 to Bjorn et al.

For a number of practical and economic reasons, most clinical applications have been based on murine antihuman monoclonal antibodies. Murine antibodies can be raised against molecules which are particularly associated with neoplastic cells using techniques known in the art. In this regard, tumor cells express increased numbers of various receptors for molecules which augment their proliferation (Goustin et al. (1986) *Cancer Res.* 46:1015–1029), many of which receptors are the products of oncogenes (Cline et al. (1984) *Ann Intern Med.* 101:223–228). Thus, a number of monoclonal antibodies directed against receptors for transferrin (Taetle et al. (1987) *Cancer Res.* 47:2040–2044 and Sauvage et al. (1987) *Cancer Res.* 47:747–753), interleukin-2 (Waldmann, T. A. (1986) *Science* 232:727–732 and Wong, et al. (1987) *J. Exp Med.* 166:1055–1069), and epidermal growth factor (Masui et al. (1984) *Cancer Res.* 44:1002–1007, Sato et al. (1983) *Mol Biol Med.* 1:511–529, and Rodeck et al. (1987) *Cancer Res.* 57:3692–3696) have been described. Although such molecules have antigen binding specificities of significant therapeutic value, the use of such murine antibodies in the treatment of human neoplastic disease has been limited since those molecules are immunogenic to the human immune system.

A number of investigators have used monoclonal antibodies as carriers of cytotoxic substances in attempts to selectively direct those agents to malignant tissue. In this manner, radioisotopes, natural toxins, chemotherapy agents, or other substances (such as biological response modifiers) are chemically linked or conjugated to a monoclonal antibody to form "immunoconjugates" and "immunotoxins." More particularly, a number of monoclonal antibodies have been conjugated to toxins such as ricin, abrin, diphtheria toxin and Pseudomonas exotoxin or to enzymatically active portions (A chains) thereof via heterobifunctional agents. See, e.g., U.S. Pat. No. 4,753,894 to Frankel et al.; Nevelle, et al. (1982) *Immunol Rev* 62:75–91; Ross et al. (1980) *European J Biochem* 104; Vitteta et al. (1982) *Immunol Rev* 62:158–183; Raso et al. (1982) *Cancer Res* 42:457–464, and Trowbridge et al. (1981) *Nature* 294:171–173. However, several factors have limited therapy using immunoconjugates or immunotoxins, particularly the production of human antimurine antibodies which greatly lowers the therapeutic index associated with those agents.

A number of cells which are capable of developing resistance to drugs have been identified. Hamster, mouse and human tumor cell lines displaying multiple-drug resistance (MDR) have been reported. A major problem in the chemotherapy of cancer is the development of cross-resistance of some human tumors to multiple chemotherapeutic drugs. This type of multiple-drug resistance is accompanied by a decrease in drug accumulation and an increase in the expression of a multiple drug resistance protein, which is also known as P-glycoprotein or gp170. Throughout this patent application, the term "P-glycoprotein" shall denote both P-glycoprotein and gp170. P-glycoprotein is a high molecular weight membrane protein (Mw 170–180 kDa) encoded by the MDR1 gene which is often amplified in MDR cells. The MDR1 gene has been cloned, and the complete nucleotide sequence of the coding region of the human MDR1 gene has been determined (see, e.g., U.S. Pat. Nos. 4,912,039, to Riordon, and 5,206,352, to Roninson). A method of isolating cDNA specific for P-glycoprotein is described in European Patent Publication No. 174,810, published 3 Mar. 1986.

While the "classical" MDR is based on P-glycoprotein, the "non-classical" MDR is based on other mechanisms, some of them as yet undefined. Throughout this patent application, the collective term "MDR phenotype" shall include both the classical and non-classical MDR phenotypes. "MDR markers" or "MDR antigens" include P-glycoprotein and other antigens expressed solely or differentially on cells expressing the MDR phenotype. Different mutant cell lines exhibit different degrees of drug resistance. Examples of cell lines exhibiting the MDR phenotype have been selected for resistance to a single cytotoxic agent. These cell lines also display a broad, unpredictable cross-resistance to a wide variety of unrelated cytotoxic drugs having different chemical structures and targets of action, many of which are used in cancer treatment. This resistance impedes the efficacy of drugs used in chemotherapy to slow down or decrease the multiplication of cancerous cells. Accordingly, there has been an interest in providing monoclonal antibodies which are capable of selectively binding tumor cells expressing the MDR phenotype. Such antibodies can be used to prepare immunoconjugates for targeting toxins or other moieties to MDR cells.

A monoclonal antibody that is capable of recognizing the K562/ADM adriamycin-resistant strain of a human myelogenous leukemia cell line K562 has been disclosed in European Patent Publication No. 214,640 A3, published 18 Mar. 1987. This monoclonal antibody is produced by a hybridoma formed as a fusion product between a mouse myeloma cell and a spleen cell from a mouse that has been immunized with the K562/ADM strain.

Because of the immunogenicity problems associated with the therapeutic use of murine antibody molecules, a number of chimeric antibodies composed of human and non-human amino acid sequences have been proposed. Particularly, hybrid antibody molecules having variable regions derived from, for example, a murine immunoglobulin fused to constant regions derived from a human immunoglobulin have been described. See e.g., U.S. Pat. No. 4,816,567; Winter et al. (1991) *Nature* 349:293–299; and Lobuglio et al. (1989) *Proc. Nat. Acad. Sci. USA* 86:4220–4224. Further, since constant regions are not required for antigen recognition or binding, antibody fragments such as F(ab), F(ab')$_2$ and Fv which do not comprise the Fc portion have been indicated as useful in radioimmunodetection, or as candidates for conjugation to a large toxin subunit such as ricin A-chain to provide a less immunogenic immunotoxin with an appreciable serum half-life. Dillman, R. O. (1989) *Ann Intern Med.* 111(7):592–603.

A number of recombinant or biosynthetic molecules comprising rodent antigen-binding sites have been described. Particularly, molecules having rodent antigen-binding sites built directly onto human antibodies by grafting only the rodent binding site, rather than the entire variable domain, into human immunoglobulin heavy and light chain domains have been described. See, e.g., Riechmann et al. (1988) *Nature* 332:323–327 and Verhoeyen et al. (1988) *Science* 239:1534–1536. Molecules having an antigen-binding site wherein at least one of the complementarity determining regions (CDRs) of the variable domain is derived from a murine monoclonal antibody and the remaining immunoglobulin-derived parts of the molecule are derived from human immunoglobulin have been described in U.K Patent Publication No. GB 2,276,169, published 21 Sep. 1994. A number of single chain antigen-binding site polypeptides and single chain Fv (sFv) molecules have also been described. See, e.g., U.S. Pat. Nos. 5,132,405 and 5,091,513 to Huston et al.; and 4,946,778 to Ladner et al.

SUMMARY OF THE INVENTION

It is an object of the invention to provide novel compositions that are derived from antigen-binding sites of immunoglobulins having affinity for cancer antigens. In one aspect of the invention, nucleotide sequences encoding complementarity determining regions ("CDRs") and framework regions ("FRs") derived from variable domains of heavy ("$V_H$") and light ("$V_L$") chains of monoclonal antibodies capable of binding specifically to a human tumor cell displaying a multiple-drug resistance ("MDR") phenotype are used in the design and construction of molecules which exhibit immunological binding properties of antibody antigen-binding sites.

In one particular embodiment, a nucleic acid molecule is provided which includes a plurality of nucleotide sequences that encode a monomeric polypeptide. The monomeric polypeptide includes a group of amino acid residues that are homologous to one or more CDRs derived from a $V_H$ or a $V_L$ domain of an antibody capable of binding specifically to a tumor cell displaying a MDR phenotype. The CDR residues are interposed between groups of flanking amino acid residues that impart a three-dimensional structure to the molecule, wherein the CDR residues are displayed as projecting loops which form an antigen-binding surface. In one particular embodiment, the flanking amino acid residues are homologous to one or more FRs derived from a $V_H$ or a $V_L$ domain of an antibody capable of binding specifically to a tumor cell displaying a MDR phenotype.

In various related embodiments, monomeric polypeptides are provided that include a group of amino acid residues that are homologous to one, two, or a set of three CDRs derived from a heavy or light chain of an antibody molecule. Further, monomeric polypeptides are provided that include a group of amino acid residues that are homologous to one, two, three, or a set of four FRs derived from a heavy or light chain of an antibody molecule. Thus, in particular aspects of the invention, nucleic acid molecules are provided that include nucleotide sequences that are substantially homologous to the nucleotide sequence of a single $V_H$ or $V_L$ domain of an antibody capable of binding specifically to a tumor cell displaying a MDR phenotype. The polypeptides encoded by those molecules are capable of exhibiting immunological binding properties of antigen-binding sites.

It is a further object of the invention to use molecular biology techniques to provide nucleic acid molecules encoding synthetic or recombinant moieties derived from the above-described molecules and exhibiting altered or enhanced antigen-binding capabilities, reduced immunogenicity, or combinations thereof. In one particular embodiment, nucleic acid molecules are provided wherein nucleotide sequences encoding various CDRs can be switched or replaced to provide a synthetic variable domain molecule which displays an altered antigen binding specificity.

In various related embodiments, synthetic nucleic acid molecules are provided that include nucleotide sequences that encode one or more CDRs flanked by recombinantly engineered regions. In one particular embodiment, synthetic nucleic acid molecules are provided including sequences encoding a $V_H$ or $V_L$ domain molecule featuring a CDR set derived from a murine antibody molecule that is capable of binding specifically to a human tumor cell displaying a MDR phenotype, wherein the murine CDR set is supported by flanking FRs derived from a human immunoglobulin molecule. In another embodiment, synthetic nucleic acid molecules are provided including nucleotide sequences encoding a $V_H$ or $V_L$ domain molecule including a CDR set derived from a murine antibody molecule that is capable of binding specifically to a human tumor cell displaying a MDR phenotype, wherein the murine CDR set is supported by flanking recombinantly veneered FRs. The recombinantly veneered FRs include a first group of amino acid residues that are homologous to residues derived from a variable region of a heavy or light chain of a murine immunoglobulin, wherein those residues include canonical residues, buried residues, substantially buried residues, interdomain contact residues, and residues directly adjacent to a CDR. The veneered FRs further include a second group of amino acid residues that are homologous to residues derived from FRs of a variable region of a heavy or light chain of a human immunoglobulin.

It is yet a further object of the invention to provide a process for producing the above-described monomeric $V_H$ or $V_L$ domain molecules. Thus, in one embodiment, an expression cassette is provided which includes a nucleic acid molecule encoding a $V_H$ or $V_L$ domain molecule operably linked to a control sequence capable of directing the expression of the nucleic acid molecule. In this manner, expression of the variable domain molecules can be readily effected in a suitable host cell using methods well known in the art. In a related embodiment, a coexpression system is established whereby nucleic acid molecules encoding for complementary monomeric $V_H$ and $V_L$ domain molecules are expressed at substantially the same rate in a suitable host cell. In yet a further related embodiment, a coexpression system is used to produce non-covalent heterodimer molecules that exhibit immunological binding properties of an immunoglobulin which binds to a human tumor cell displaying a MDR phenotype. The subject heterodimer is formed by the coexpression of complementary $V_H$ and $V_L$ domain molecules in a transfected host cell wherein the coexpressed polypeptides dimerize under the influence of non-covalent interdomain contacts to form an antigen-binding site.

It is another object of the invention to provide biosynthetic single-chain Fv ("sFv") molecules which include an antigen-binding site that exhibits immunological binding properties of an antibody capable of binding specifically to a human tumor cell displaying a MDR phenotype. In one embodiment, sFv molecules are provided having at least two polypeptide domains connected by a polypeptide linker spanning the distance between the C-terminus of one domain and the N-terminus of the other, wherein each of the polypeptide domains includes amino acid residues homologous to a set of CDRs interposed between a set of FRs such that the CDRs are capable of participating in immunological binding activity.

In various related embodiments, nucleic acid molecules are provided including nucleotide sequences encoding sFv molecules having re-paired CDRs or CDR sets, molecules which combine murine CDRs with supporting human FRs, or molecules which feature murine CDRs supported by flanking recombinantly veneered FRs that have been assembled as described above.

In yet further related embodiments, nucleic acid molecules are provided which include nucleotide sequences encoding sFv molecules having a third polypeptide domain. The third polypeptide domain is joined either to the first or the second domain by a further polypeptide linker moiety spanning the distance between the C-terminus or N-terminus of one of the first or second domains, and the N-terminus or C-terminus, respectively, of the third polypeptide domain. In particular embodiments, the third polypeptide domain comprises a second antigen-binding site formed as previously described. In other embodiments, the third polypeptide domain comprises an ancillary polypeptide chain that is bioactive, such as a cytokine, toxin, ligand, hormone or enzyme, or the third domain provides a site on which a toxin, drug or remotely detectable moiety can be attached. Thus the various embodiments are useful in specific binding assays, affinity purification techniques, drug or toxin targeting, tumor imaging, and immunological and genetic therapeutics for various cancers.

It is a further related object of the invention to provide expression cassettes which include nucleotide sequences encoding the novel sFv molecules and sFv molecules with ancillary polypeptide regions as just described. The sFv polypeptides can be expressed in suitable prokaryotic and eukaryotic host cells using techniques that are well known in the art.

BRIEF DESCRIPTION OF THE FIGURES

FIG. 1 (SEQ ID NOS:15 and 16) shows the nucleotide sequence and the predicted amino acid sequence of the $V_H$ encoding domain derived from a 15D3 hybridoma. Proceeding from the N-terminus, the sequences of the three CDRs are generally indicated HCDR1, HCDR2 and HCDR3. Also proceeding from the N-terminus, the sequences of the four FRs are generally indicated at HFR1, HFR2, HFR3 and HFR4.

FIG. 2 (SEQ ID NOS:17 and 18) shows the nucleotide sequence and the predicted amino acid sequence of the $V_L$ encoding domain derived from a 15D3 hybridoma. Proceeding from the N-terminus, the sequences of the three CDRs are generally indicated LCDR1, LCDR2 and LCDR3. Also proceeding from the N-terminus, the sequences of the four FRs are generally indicated at LFR1, LFR2, LFR3 and LFR4.

DETAILED DESCRIPTION OF THE INVENTION

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

An "antigen" includes any substance that may be specifically bound by an antibody molecule. Thus, the term "antigen" encompasses biologic molecules including, but not limited to, simple intermediary metabolites, sugars, lipids, autoacids, and hormones, as well as macromolecules such as complex carbohydrates, phopholipids, nucleic acids and proteins.

An "immunogen" is a macromolecular antigen that is capable of initiating lymphocyte activation resulting in an antigen-specific immune response. An immunogen therefore includes any molecule which contains one or more epitopes that will stimulate a host's immune system to initiate a secretory, humoral and/or cellular antigen-specific response.

The term "antibody" encompasses polyclonal and monoclonal antibody preparations, as well as preparations including hybrid antibodies, altered antibodies, F(ab')$_2$ fragments, F(ab) fragments, Fv fragments, single domain antibodies, chimeric antibodies, humanized antibodies, and functional fragments thereof which exhibit immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')$_2$, Fv, and other fragments that exhibit immunological binding properties of the parent monoclonal antibody molecule.

Methods of making polyclonal and monoclonal antibodies are known in the art. Polyclonal antibodies are generated by immunizing a suitable animal, such as a mouse, rat, rabbit, sheep or goat, with an antigen of interest. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof.

Rabbits, sheep and goats are preferred for the preparation of polyclonal sera when large volumes of sera are desired. These animals are good design choices also because of the availability of labeled anti-rabbit, anti-sheep and anti-goat antibodies. Immunization is generally performed by mixing or emulsifying the antigen in saline, preferably in an adjuvant such as Freund's complete adjuvant ("FCA"), and injecting the mixture or emulsion parenterally (generally subcutaneously or intramuscularly). The animal is generally boosted 2–6 weeks later with one or more injections of the antigen in saline, preferably using Freund's incomplete adjuvant ("FIA"). Antibodies may also be generated by in vitro immunization, using methods known in the art. Polyclonal antisera is then obtained from the immunized animal.

Monoclonal antibodies are generally prepared using the method of Kohler and Milstein, *Nature* (1975) 256:495–497, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

The "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439–473.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659–2662; Hochman et al. (1976) Biochem 15:2706–2710; and Ehrlich et al. (1980) Biochem 19:4091–4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and 4,946,778, to Ladner et al.

Each of the above-described molecules includes a heavy chain and a light chain CDR set, respectively interposed between a heavy chain and a light chain FR set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3," respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349:293–299; Lobuglio et al. (1989) *Proc. Nat. Acad. Sci. USA* 86:4220–4224; Shaw et al. (1987) *J Immunol.* 138:4534–4538; and Brown et al. (1987) *Cancer Res.* 47:3577–3583), rodent CDRs grafted into a human supporting FR prior to fusion with an appropriate human antibody constant domain (Riechmann et al. (1988) *Nature* 332:323–327; Verhoeyen et al. (1988) *Science* 239:1534–1536; and Jones et al. (1986) *Nature* 321:522–525), and rodent CDRs supported by recombinantly veneered rodent FRs (European Patent Publication No. 519,596, published 23 Dec. 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) *Ann. Rev. Biochem.* 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in *Sequences of Proteins of Immunological Interest*, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. The term "domain," or "polypeptide domain" refers to that sequence of a polypeptide that folds into a single globular region in its native conformation, and that may exhibit discrete binding or functional properties.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, preferably at least 4–7 amino acids, more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition. Thus, for example, an isolated nucleic acid molecule which encodes a particular CDR polypeptide consists essentially of the nucleotide coding sequence for the subject molecular recognition unit.

"Homology" refers to the percent of identity between two polynucleotide or polypeptide moieties. The correspondence between the sequence from one form to another can be determined by techniques known in the art. For example, homology can be determined by a direct comparison of the sequence information between two polypeptide molecules. Alternatively, homology can be determined by hybridization of polynucleotides under conditions which form stable duplexes between homologous regions (for example, those which would be used prior to $s_1$ digestion), followed by digestion with single-stranded specific nuclease(s), followed by size determination of the digested fragments. Two DNA or polypeptide sequences are "substantially homologous" when at least about 80% (preferably at least about 90%, and most preferably at least about 95%) of the nucleotides or amino acids match over a defined length of the molecule.

The terms "recombinant DNA molecule," or "recombinant nucleic acid molecule" are used herein to refer to a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, the term encompasses "synthetically derived" nucleic acid molecules.

The term "nucleic acid molecule" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

A "coding sequence" is a nucleic acid molecule which is translated into a polypeptide, usually via mRNA, when placed under the control of appropriate regulatory sequences. The boundaries of the coding sequence may be determined by a translation start codon at the 5'-terminus and a translation stop codon at the 3'-terminus. A coding sequence can include, but is not limited to, cDNA, and recombinant nucleotide sequences.

"Control sequence" refers to nucleic acid sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression of a coding sequence, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

By "vector" is meant any genetic element, such as a plasmid, phage, transposon, cosmid, chromosome, virus etc., which is capable of replication when associated with the proper control elements and which can transfer gene sequences between cells. Thus, the term includes cloning and expression vehicles, as well as viral vectors.

"Transfection" refers to the uptake of foreign DNA by a cell, and a cell has been "transfected" when exogenous DNA has been introduced inside the cell membrane. In this manner, the exogenous DNA may or may not be integrated (covalently linked) to chromosomal DNA making up the genome of the cell. In procaryotes and yeasts, for example, the exogenous DNA can be maintained on an episomal element, such as a plasmid. With respect to the invention, a eucaryotic cell is "stably transfected" when exogenous DNA has become integrated into the cellular genome so that it is inherited by daughter cells through chromosome replication. This stability is demonstrated by the ability of the eucaryotic cell to establish cell lines or clones comprised of a population of daughter cells containing the exogenous DNA. "Transient transfection" refers to cases where exogenous DNA does not remain in the cells for an extended period of time, e.g., where plasmid DNA is transcribed into mRNA and translated into protein without integration into the host cell genome.

A "host cell" is a cell which has been transfected, or is capable of transfection, by an exogenous DNA sequence using methods within the skill of those in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) Gene 13:197. More particularly, there are two major steps in transfection: first, the exogenous DNA must traverse the recipient (host) cell plasma membrane in order to be exposed to the cell's transcription and replication machinery; and second, the DNA must either become stably integrated into the host cell genome, or be capable of extrachromosomal replication at a sufficient rate. A number of transfection methods have been described in the art, such as calcium phosphate co-precipitation (Graham et al. (1973) *Virol.* 52:456–467), direct micro-injection into cultured cells (Capecchi, M. R. (1980) *Cell* 22:479–488), electroporation (Shigekawa et al. (1988) *BioTechniques* 6:742–751), liposome mediated gene transfer (Mannino et al. (1988) *BioTechniques* 6:682–690), lipid-mediated transfection (Felgner et al. (1987) *Proc. Natl. Acad. Sci. USA* 84:7413–7417), and nucleic acid delivery using high-velocity microprojectiles (Klein et al. (1987) *Nature* 327:70–73).

"Gene transfer" or "gene delivery" refers to methods or systems for reliably inserting foreign DNA into host cells such that the transferred genetic material is stable with respect to the loci of insertion and is also susceptible of expression by the host cells. Such methods provide a unique approach for the treatment of acquired and inherited diseases. A number of systems have been developed for gene transfer into mammalian cells. See, e.g., U.S. Pat. No. 5,399,346.

B. General Methods

Initially, mammalian immunoglobulin molecules capable of binding specifically to a human tumor cell displaying a MDR phenotype were produced to provide antigen-binding sites for use under the invention. More particularly, monoclonal antibodies capable of binding specifically to a human tumor cell which over-expresses P-glycoprotein were produced as follows.

Murine fibroblast cell lines were used as live whole cell immunogens. These cell lines were obtained from Dr. Igor Roninson at the University of Illinois, Chicago Medical Center. The cell lines were Balb/c 3T3 fibroblast cells, which were transfected with the human MDR1 gene and then selected for the drug resistance phenotype by growing them in vinblastine-containing culture medium (designated BATV.2 to indicate that the cells had been grown in and were resistant to 0.2 $\mu$g/ml of vinblastine drug). For immunizations, five million live drug resistant cells were inoculated intra-peritoneally into six-week old male Balb/c mice, which had been injected intra-peritoneally with thirty million drug-sensitive parent 3T3 fibroblast cells (BA3T3) 24 hours after birth to induce neonatal tolerization against parent cell antigens. The adult mice were boosted at two-week and six-week intervals, by intra-peritoneal injections with five million BATV.2 cells. Three days after the last intravenous boost, the spleens were removed for cell fusion.

Somatic cell hybrids were prepared by the method of Buck et al. (1982) In Vitro 18:377–381, using the azaguanine resistant, non-secreting murine myeloma cell line SP2/0-Ag14 (obtained from the American Type Culture Collection, designated under cell repository line number ATCC CRL1581). 96-well polystyrene flat-bottom microtiter plates were used. One thousand five hundred wells were generated from those fusions, of which one thousand and fifty exhibited hybridoma growth.

The hybridoma supernatants were assayed for reactive antibody in either a solid phase ELISA or an indirect immunofluorescence assay both with the immunizing BATV.2 cell line and the parent BA3T3 cell line. For the solid phase ELISA, each 96-well polyvinylchloride (PVC) flat-bottom microtiter plate was coated with 50 $\mu$l per well of a prewashed cell suspension at $2\times10^6$ viable cells/well. Plates were centrifuged for 5 minutes at 900×g. To each well was added 50 $\mu$l of 0.5% glutaraldehyde in cold phosphate buffered saline (PBS) and the cells were incubated for 15 minutes at room temperature. The cells were then washed twice in PBS and filled with 100 mM glycine in 0.1% bovine serum albumin (BSA) for 30 minutes at room temperature. After washing twice with PBS, the wells were incubated with 50 $\mu$l of hybridoma supernatant (either neat or diluted) for 1 hour at room temperature. After washing three times with PBS, 100 $\mu$l of a 1:200 dilution of peroxidase-conjugated goat anti-mouse IgG was added to each well. The diluent was PBS with 0.1% BSA. The wells were then washed with PBS and reacted with 100 $\mu$l of O-phenylenediamine substrate (0.5 mg/ml in 0.1M citrate buffer pH 6.5 with 0.5 $\mu$l/ml $H_2O_2$) for 5 to 15 minutes at room temperature. The reaction was quenched with 100 $\mu$l of 1N HCl. Optical density was measured at 495 nm on a Micro-ELISA reader (Flow Lab., Inc., McLean, Va.). The background was 0.1±0.1 optical density units using medium without mouse monoclonal antibody. Wells that gave a reaction on the BATV.2 cells that was at least 2-fold greater than the reaction with BA3T3 cells were saved for cloning. 6.7% of all the hybridomas tested were saved for cloning.

Clones from the hybridomas selected by the solid phase ELISA assay were then subjected to indirect immunofluorescence cell line assay. 100,000 BATV.2 cells of the immunizing cell line (and other drug-resistant lines) were seeded overnight with appropriate medium in each chamber of a set of 8 chambered slides. The other drug-resistant cell lines were: KB-A1, KB-C1, and KB-V1. The parental cell line KB-3-1 which was sensitive to all three drugs was also used. The KB-A1, KB-C1, and KB-V1 cell lines were obtained from Ira Pastan of National Cancer Institute (NCI) of the National Institute of Health (NIH), Bethesda, Md. The cells were washed with PBS containing 0.1% BSA. The slides of either cell type were incubated with 1:10 dilutions of hybridoma supernatant for 30 minutes at 4° C. The cells were again washed and incubated at 4° C. for 30 minutes with a 1:50 dilution of fluorescein isothiocyanate (FITC)-conjugated goat F(ab')$_2$ anti-mouse IG. The cells were washed three times, fixed in 1.5% formaldehyde in PBS for 5 minutes, and the chambers were removed and the slides were rinsed in PBS. The slides were then mounted and examined with a fluorescence microscope. Hybridomas which produced MABs that showed strong fluorescent binding to drug-resistant cells but little or no detectable fluorescent binding to drug-sensitive cells were saved.

Thirteen hybridoma wells revealed such specificity in this screen. These wells gave a reaction on the resistant cell lines that was at least 2-fold greater than the reaction with the KB-3-1 cells. Hybridoma 15D3 was selected from one of these thirteen wells.

The sequences of the variable regions from the heavy ($V_H$) and light ($V_L$) chains of a monoclonal antibody produced by the hybridoma cell line 15D3 were determined as follows. RNA encoding the heavy and light chains of a 15D3 immunoglobulin was extracted from the subject 15D3 hybridomas using standard methods involving cellular solubilization with guanidinium isothiocyanate (Chirgwin et al. (1979) Biochem. 18:5294–5299). The mRNA was then used to prepare cDNA for subsequent isolation. of $V_H$ and $V_L$ genes by PCR methodology known in the art (Sambrook et al., eds., Molecular Cloning (1989) Cold Spring Harbor laboratories Press, NY). The N-terminal amino acid sequence of the heavy and light chains can be independently determined by automated Edman sequencing. Further stretches of the CDRs and flanking FRs can also be determined by amino acid sequencing of the $V_H$ and $V_L$ fragments if necessary. Such sequence analysis is now conducted routinely. Synthetic primers were then designed for isolation of the $V_H$ and $V_L$ genes from the 15D3 monoclonal antibodies and the isolated genes were ligated into an appropriate vector for sequencing, such as pBK-CMV, available from Stratagene (San Diego, Calif.) or the sequencing vector pUC19 (Yanisch-Perron (1985) Gene 33:103), available from ATCC (Rockville, Md.).

A sequencing method, particularly, the Applied Biosystems Taq DYEDEOXY TERMINATOR CYCLE SEQUENCING® method, was used to determine the sequences of the CDRs and FRs from the $V_H$ and $V_L$ domain of 15D3 monoclonal antibodies. The method involves sequential enzymatic chain extension and termination reactions to produce a set of nested fragments which, when resolved, yield data from which a DNA sequence can readily be ascertained. Such techniques have been described in the art. See, e.g., Applied Biosystems Taq Dye Deoxy Terminator Cycle Sequencing P/N 901497, Rev. E; Connell et al. (1987) BioTechniques 5:342–348; Sanger et al. (1977) Proc. Natl. Acad. Sci. USA 74:5463–5467; Smith et al. (1986) Nature 321:674–679; and Gelfand, D. H. (1989) "Taq DNA polymerase", in PCR Technology, Principles and Applications for DNA Amplification (H. A. Erlich, ed.), Stockton Press, New York. The major steps of the method entail: (1) denaturation; (2) annealing; (3) chain extension; (4) chain termination; (5) several repeats of steps 1–4 to generate more fragments; (6) gel electrophoresis; and (7) detection. Denaturation involves separation of the template strands by exposure to heat. Annealing involves the hybridization of a synthetic oligonucleotide primer with the template DNA. By means of Taq polymerase, a synthetic DNA strand starting from the 3' end of the primer is enzymatically formed in the presence of four deoxynucleotide triphosphates (dNTP) and four dideoxynucleotide triphosphates (ddNTP) which are labeled with a dye specific for each base. The DNA strand is either elongated or terminated by the incorporation of dNTP or ddNTP, respectively. The double stranded molecules created can be used as "templates" for further cycles. After an optimal number of cycles, gel electrophoresis is used to resolve the synthesized DNA fragments. The DNA fragments on the gel are then detected by fluorescence in an ABI 373 Sequencer®, and the signals are analyzed by computer. With each primer, approximately 300 bases can be read.

The nucleic acid sequence and the predicted amino acid sequence of the $V_H$ encoding domain derived from a 15D3 antibody are depicted in FIG. 1. Proceeding from the amino terminus, the sequences of the three CDRs are generally indicated at HCDR1, HCDR2 and HCDR3; and the sequences of the four FRs are generally indicated at HFR1, HFR2, HFR3 and HFR4.

The individual nucleic acid sequences of the three CDRs (HCDR1, HCDR2 and HCDR3), and the nucleic acid sequences of the four FRs (HFR1, HFR2, HFR3 and HFR4) from the $V_H$ region of a 15D3 antibody are set forth in Table 1 as (SEQ ID NOS:1–7)

TABLE 1

| DOMAIN | REGION | SEQ ID NO: | SEQUENCE |
|---|---|---|---|
| $V_H$ | HCDR1 | (SEQ ID NO: 1) | AGGTATACCATGTCT |
| $V_H$ | HCDR2 | (SEQ ID NO: 2) | ACCATTAGTAGTGGTGGTGGTAACACCTACTATCCAGAC AGTGTGAAGGGT |
| $V_H$ | HCDR3 | (SEQ ID NO: 3) | TACGGGGCTGGTGACGCCTGGTTTGCTTAC |
| $V_H$ | HFR1 | (SEQ ID NO: 4) | GAGGTGAAGGTTGTGGAGTCTGGGGGAGTCTTAGTGAGG CCTGGAGGGTCCCTGAAACTCTCCTGTGCAGCCTCTGGA TTCACTTTCAGT |
| $V_H$ | HFR2 | (SEQ ID NO: 5) | TGGGTTCGCCAGACTCCGGAGAAGCGGCTGGAGTGGGTC GCA |
| $V_H$ | HFR3 | (SEQ ID NO: 6) | CGATTCACCGTCTCCAGAGACAATGCCATGAGCAGCCTG TACCTGCAAATGAGCAGTCTGAGGTCTGAGGACACGGCC TTGTATTACTGTGCAAGA |
| $V_H$ | HFR4 | (SEQ ID NO: 7) | TGGGGCCAAGGGACTCTGGTCACAGTTTCTGCA |

The nucleic acid sequence and the predicted 20 amino acid sequence of the $V_L$ encoding domain derived from a 15D3 antibody are depicted in FIG. 2. Proceeding from the amino terminus, the sequences of the three CDRs are generally indicated at LCDR1, LCDR2 and LCDR3; and the sequences of the four FRs are generally indicated at LFR1, LFR2, LFR3 and LFR4.

The individual nucleic acid sequences of the three CDRs (LCDR1, LCDR2 and LCDR3), and the nucleic acid sequences of the four FRs (LFR1, LFR2, LFR3 and LFR4) from the $V_L$ region of a 15D3 antibody are set forth in Table 2 as (SEQ ID NOS:8–14)

TABLE 2

| DOMAIN | REGION | SEQ ID NO: | SEQUENCE |
|---|---|---|---|
| $V_L$ | LCDR1 | (SEQ ID NO: 8) | AGATCCAGTCAGAGCATTGTGCATAGTACTGGAAACACC TATTTAGAG |
| $V_L$ | LCDR2 | (SEQ ID NO: 9) | AAAGTTTCCAACCGATTTTCT |
| $V_L$ | LCDR3 | (SEQ ID NO: 10) | TTTCAAGGTTCACATTTTCCTCGGACG |
| $V_L$ | LFR1 | (SEQ ID NO: 11) | GAGCTCGCGATGACCCAGACTCCACTCTCCCTGCCTGTC AGTCTTGGAGATCAAGCCTCCATCTCTTGC |
| $V_L$ | LFR1 | (SEQ ID NO: 12) | TGGTACCTGCAGAAACCAGGCCAGTCTCCAAAGCTCCTG ATCTAC |
| $V_L$ | LFR3 | (SEQ ID NO: 13) | GGGGTCCCAGACAGGTTCAGTGGCAGTGGATCAGGGACA GATTTCACACTCAAGATCAGTAGACTGGAGGCTGAGGAT CTGGGAGTTTATTACTGC |
| $V_L$ | LFR4 | (SEQ ID NO: 14) | TTCGGTGGAGGCACAGGCTGGAAATCAAG |

Thus, one aspect of the invention involves the design and construction of a nucleic acid molecule comprising a plurality of nucleotide sequences which encode a monomeric polypeptide. The monomeric polypeptide exhibits immunological binding properties of an immunoglobulin which binds to a human tumor cell displaying the MDR phenotype. More particularly, the polypeptide includes a group of amino acid residues that are homologous to a set of CDRs derived from a variable region of a heavy or light chain of an antibody capable of binding specifically to a tumor cell which over-expresses P-glycoprotein antigens, wherein the CDRs are interposed between flanking FR amino acid residues also derived from a variable region of a heavy or light chain of an antibody molecule.

In one particular embodiment, a nucleic acid molecule is provided which comprises a nucleotide sequence which is substantially homologous to the nucleotide sequence of a single $V_H$ domain derived from a 15D3 antibody, which sequence is depicted in FIG. 1. In this manner, the nucleic acid molecule encodes a monomeric heavy chain variable domain polypeptide (e.g., half of an Fv comprising a single CDR set specific for an antigen interposed by a single flanking FR set) which has the ability to recognize and bind antigen, although at lower affinity than an entire antigen-binding site. See, e.g., Painter et al. (1972) Biochem. 11:1327–1337. The three CDRs (e.g., HCDR1, HCDR2 and HCDR3) in the monomeric variable domain polypeptide interact to define an antigen-binding region. The FRs flanking the CDRs impart a tertiary structure to the molecule which is essentially conserved in native human and murine immunoglobulins.

In another particular embodiment, a nucleic acid molecule is provided which comprises a nucleotide sequence which is substantially homologous to the nucleotide sequence of a single $V_L$ domain derived from a 15D3 antibody, which sequence is depicted in FIG. 2. In this manner, the nucleic acid molecule encodes a monomeric light chain variable domain which also has the ability to recognize and bind antigen. The three CDRs (e.g., LCDR1, LCDR2 and LCDR3) in the monomeric variable domain polypeptide interact to define an antigen-binding region which is supported by the flanking FRs.

In a further aspect of the invention, a process for producing a monomeric heavy or light chain variable domain polypeptide is provided. Initially, an expression cassette is provided which comprises a nucleic acid molecule encoding either the $V_H$ or $V_L$ molecule described above operably linked to a control sequence capable of directing the expression of the nucleic acid molecule. The expression cassette may further include an origin of replication for autonomous replication in a suitable host cell, one or more selectable markers, one or more restriction sites, a potential for high copy number and a strong promoter.

The expression cassette is placed into a suitable vector using molecular biology techniques well known in the art. See, e.g., Sambrook, et al., *Molecular Cloning: A Laboratory Manual* (2nd Edition, 1989); Maniatis et al., *Molecular Cloning: A Laboratory Manual* (1982); and *DNA Cloning: A Practical Approach*, vol. I & II (D. Glover, ed.). Suitable vectors include, but are not limited to, plasmids, phages, transposons, cosmids, chromosomes or viruses which are capable of replication when associated with the proper control elements and which can transfer the variable region gene sequences between cells.

Nucleic acid molecules comprising nucleotide sequences which are substantially homologous to either the nucleotide sequence of a single $V_H$ or $V_L$ domain derived from a 15D3 antibody can thus be stably integrated into a host cell genome or maintained on a stable episomal element in a suitable host cell using various gene delivery techniques well known in the art. See, e.g., U.S. Pat. No. 5,399,346.

In yet a further embodiment of the invention, a coexpression system can be established in a suitable host cell. "Coexpression" as used herein refers to the expression of two or more polypeptides in a host cell. Thus, one such system comprises nucleic acid molecules encoding for monomeric $V_H$ and $V_L$ domain polypeptides which are harbored in a single plasmid, either under the control of the same regulatory elements or under the control of separate elements. Similarly, monomeric variable domain polypeptides expressed from the same vector but driven by separate regulatory elements would also be considered "coexpressed." In one particular embodiment, a coexpression system is provided by the expression of two or more polypeptides from separate constructs.

More particularly, suitable host cells can be transfected with two vectors; the first vector containing an expression cassette which includes nucleotide sequences substantially homologous to a nucleotide sequence encoding a $V_H$ domain polypeptide derived from a 15D3 antibody, and the second vector containing an expression cassette which includes nucleotide sequences substantially homologous to a nucleotide sequence encoding a $V_L$ domain polypeptide derived from a 15D3 antibody. Generally, the vectors are identical—except in so far as the coding sequences and selectable markers are concerned—so as to ensure that the $V_H$ and $V_L$ polypeptides are substantially equally expressed in the transfected host cell.

In this manner, a non-covalent heterodimer which exhibits immunological binding properties of an immunoglobulin which binds to a human tumor cell displaying a MDR phenotype can be readily produced using a coexpression system. More particularly, a heterodimer can be formed by the coexpression of complementary $V_H$ and $V_L$ polypeptides in a transfected host cell. The coexpressed polypeptides dimerize under the influence of non-covalent (e.g., electrostatic) interdomain contacts to form an antigen-binding site. The dimeric molecule thus formed is substantially homologous to an Fv fragment isolated from a native immunoglobulin. In this regard, the heterodimer comprises six CDRs (a heavy chain CDR set and a light chain CDR set) disposed relative to each other in three dimensional space to form an antigen-binding surface. The antigen-binding surface is maintained by flanking FR residues to provide an antigen-binding site which retains much of the antigen recognition and binding capabilities of a native antibody molecule.

One particular heterodimer which can be produced using the coexpression system of the invention is characterized as an antigen-binding molecule having first and second polypeptide domains which are non-covalently associated via electrostatic, hydrophobic, or other non-covalent interdomain contacts between amino acid residues present in the subject polypeptide domains. The first polypeptide domain includes a first group of amino acid residues that are homologous to a CDR set which is derived from a $V_H$ domain of an antibody capable of binding specifically to a human tumor cell displaying a MDR phenotype, wherein the first group of residues are interposed between a plurality of flanking amino acid residues that are homologous to a FR set which is also derived from a $V_H$ domain of an antibody capable of binding specifically to a human tumor cell displaying a MDR phenotype. The second polypeptide domain includes a first group of amino acid residues that are homologous to a CDR set which is derived from a $V_L$ domain of an antibody capable of binding specifically to a human tumor cell displaying a MDR phenotype, wherein the first group of residues are interposed between a plurality of flanking amino acid residues that are homologous to a FR set which is also derived from a $V_L$ domain of an antibody capable of binding specifically to a human tumor cell displaying a MDR phenotype. In one particular embodiment, the first and second polypeptide domains are derived from the $V_H$ and $V_L$ domains, respectively, of a monoclonal antibody produced by the hybridoma cell line 15D3.

Polynucleotides encoding the monomeric $V_H$ or $V_L$ polypeptides can be introduced into a suitable insect host cell for expression using baculovirus systems. Materials and methods for baculovirus/insect cell expression systems are commercially available in kit form from, inter alia, Invitrogen, San Diego Calif. ("MaxBac" kit). Baculovirus expression systems generally include a transfer vector, (e.g. a bacterial plasmid) which contains a fragment of the baculovirus genome, a wild-type baculovirus with a sequence homologous to the baculovirus-specific fragment in the transfer vector, and appropriate host insect cells. Such systems are known to those skilled in the art. See, e.g, Summers and Smith (1987) *Texas Agricultural Experiment Station Bulletin No.* 1555, (hereinafter "Summers and Smith").

A number of suitable baculovirus transfer vectors have been described and can include useful control sequences, such as the late promoter derived from the p10 protein (Vlak et al. (1988) *J. Gen. Virol.* 69:765), selectable markers, enhancer sequences and other suitable signal sequences. DNA encoding suitable signal sequences can be derived from genes for secreted insect or baculovirus proteins, such as the baculovirus polyhedrin gene (Carbonell et al. (1988) *Gene* 73:409), and leader sequences of non-insect origin, such as those derived from genes encoding human α-interferon (Maeda et al. (1985) *Nature* 315:592), human gastrin-releasing peptide (Lebacq-Verheyden et al. (1988) *Molec. Cell. Biol.* 8:3129), human IL-2 (Smith et al. (1985) *Proc. Natl Acad. Sci. USA* 82:8404), mouse IL-3 (Miyajima et al. (1987) *Gene* 58:273), and human glucocerebrosidase (Martin et al. (1988) *DNA* 7:99) to provide for secretion in insect host cells.

After insertion of coding sequences encoding the $V_H$ and/or $V_L$ molecules, a suitable host insect cell can be co-transfected with the heterologous DNA of the transfer vector and the genomic DNA of a wild-type baculovirus. Methods for introducing heterologous DNA into a desired site in the baculovirus virus are known in the art. See, e.g., Summers and Smith supra; and Smith et al. (1983) *Mol. Cell. Biol.* 3:2156. For example, the insertion can be into a gene such as the polyhedrin gene, by homologous double crossover recombination. Insertion can also be into a restriction enzyme site engineered into the desired baculovirus gene. Miller et al. (1989) Bioessays 4:91.

The newly formed baculovirus expression vector can then be packaged into an infectious recombinant baculovirus. A number of recombinant baculovirus expression vectors have been developed for infection into various insect host cells. For example, recombinant baculoviruses have been developed for, inter alia: *Aedes aegypti, Autographa californica, Bombyx mori, Drosophila melanogaster, Spodoptera frugiperda, and Trichoplusia ni.* See, e.g., International Publication No. WO 89/046699; Carbonell et al. (1985) *J. Virol.* 56:153; Wright (1986) *Nature* 321:718; Smith et al. (1983) *Molec. Cell. Biol.* 3:2156; and Fraser, et al. (1989) *In Vitro Cell. Dev. Biol.* 25:225.

Cells infected with recombinant viruses are selected and cultured. Suitable host insect cells and cell culture media are commercially available for both direct and fusion expression of heterologous polypeptides in a baculovirus/expression system, and insect cell culture technology is generally known to those skilled in the art. See, e.g., Summers and Smith, supra.

Modified insect cells can thus be readily grown in an appropriate nutrient medium which allows for stable maintenance of the plasmid(s) present in the modified insect host. Where the expression product gene is under inducible control, the host can be grown to high density, and expression induced. Alternatively, where expression is constitutive, the $V_H$ and/or $V_L$ polypeptide product will be continuously expressed into the medium, and the nutrient medium must be continuously circulated to remove the product of interest and augment depleted nutrients. The $V_H$ and/or $V_L$ polypeptide product can then be purified by such techniques as chromatography, including HPLC, affinity chromatography, ion exchange chromatography; electrophoresis; density gradient centrifugation; solvent extraction, or like methods known in the art. As appropriate, the molecules can be further purified, as required, so as to remove substantially any insect proteins which are also secreted in the medium or result from lysis of insect cells.

Polynucleotides encoding the monomeric $V_H$ or $V_L$ polypeptides can also be introduced into a suitable mammalian host cell for expression or coexpression using a number of viral based systems which have been developed for gene transfer into mammalian cells. In this regard, retroviruses provide a convenient platform for gene delivery systems. A selected nucleotide sequence encoding a $V_H$ and/or a $V_L$ domain polypeptide can be inserted into a vector and packaged in retroviral particles using techniques known in the art. The recombinant virus can then be isolated and delivered to a subject. A number of suitable retroviral systems have been described (U.S. Pat. No. 5,219,740; Miller and Rosman (1989) *BioTechniques* 7:980–990; Miller, A. D. (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Cur. Opin. Genet. Develop.* 3:102–109. A number of suitable adenovirus vectors have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51– 58; Berkner, K. L. (1988) *BioTechniques* 6:616–629; and Rich et al. (1993) *Human Gene Therapy* 4:461–476). Various adeno-associated virus (AAV) vector systems have been developed recently for gene delivery. Such systems can include control sequences, such as promoter and polyadenylation sites, as well as selectable markers or reporter genes, enhancer sequences, and other control elements which allow for the induction of transcription. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Additional viral vectors which will find use for delivering the nucleic acid molecules encoding the variable domain molecules of the present invention by gene transfer include those derived from the pox family of viruses, such as vaccinia virus and avian poxvirus. By way of example, vaccinia virus recombinants expressing the novel molecules can be constructed as follows. The DNA encoding a $V_H$ and/or a $V_L$ domain polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting $TK^{(-)}$ recombinant can be selected by culturing the cells in the presence of 5-bromodeoxyuridine and picking viral plaques resistant thereto.

A vaccinia based infection/transfection system can be conveniently used to provide for inducible, transient expression or coexpression of the $V_H$ and/or $V_L$ domain molecules in a host cell. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743–6747; Fuerst et al. *Proc. Natl. Acad. Sci. USA* (1986) 83:8122–8126.

Alternatively, Avipoxviruses, such as the fowlpox and canarypox viruses, can also be used to deliver the $V_H$ or $V_L$ domain coding sequences. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al. *J. Biol. Chem.* (1993) 268:6866–6869 and Wagner et al. *Proc. Natl. Acad. Sci. USA* (1992) 89:6099–6103, can also be used for gene delivery under the invention.

Vectors encoding the subject $V_H$ and/or $V_L$ molecules can also be packaged in liposomes prior to delivery to the vertebrate subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight *Biochim. Biophys. Acta.* (1991) 1097:1–17; and Straubinger et al. in *Methods of Enzymology* (1983), Vol. 101, pp. 512–527.

Liposomal preparations for use in the instant invention include cationic (positively charged), anionic (negatively charged) and neutral preparations, with cationic liposomes particularly preferred. Cationic liposomes have been shown to mediate intracellular delivery of plasmid DNA (Felgner et al. *Proc. Natl. Acad. Sci. USA* (1987) 84:7413–7416); mRNA (Malone et al. *Proc. Natl. Acad. Sci. USA* (1989) 86:6077–6081); and purified transcription factors (Debs et al. *J. Biol. Chem.* (1990) 265:10189–10192), in functional form.

Cationic liposomes are readily available. For example, N[1-2,3-dioleyloxy)propyl]-N,N,N-triethyl-ammonium (DOTMA) liposomes are available under the trademark LIPOFECTIN®, rom GIBCO BRL, Grand Island, N.Y. (See, also, Felgner et al. *Proc. Natl. Acad. Sci. USA* (1987) 84:7413–7416). Other commercially available liposomes include transfectase (DDAB/DOPE) and DOTAP/DOPE (Boehringer). Other cationic liposomes can be prepared from readily available materials using techniques well known in the art. See, e.g., Szoka et al. *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art. See, e.g., Straubinger et al. in *Methods of Immunology* (1983), Vol. 101, pp. 512–527; Szoka et al. *Proc. Natl. Acad. Sci. USA* (1978) 75:4194–4198; Papahadjopoulos et al. *Biochim. Biophys. Acta* (1975) 394:483; Wilson et al. *Cell* (1979) 17:77); Deamer and Bangham *Biochim. Biophys. Acta* (1976) 443:629; Ostro et al. *Biochem. Biophys. Res. Commun.* (1977) 76:836; Fraley et al. *Proc. Natl. Acad. Sci. USA* (1979) 76:3348); Enoch and Strittmatter *Proc. Natl. Acad. Sci. USA* (1979) 76:145); Fraley et al. *J. Biol. Chem.* (1980) 255:10431; Szoka and Papahadjopoulos *Proc. Natl. Acad. Sci. USA* (1978) 75:145; and Schaefer-Ridder et al. *Science* (1982) 215:166.

Thus, a number of nucleic acid molecules which comprise nucleotide sequences encoding polypeptides that are substantially homologous to $V_H$ and/or $V_L$ domains of an antibody capable of binding specifically to a human tumor cell displaying a MDR phenotype are described. The subject nucleic acid molecules may be expressed or coexpressed to provide monomeric or heterodimeric polypeptides, respectively. In particular embodiments, the polypeptides are derived from $V_H$ and/or $V_L$ domains of a monoclonal antibody produced by the 15D3 hybridoma cell line.

In another aspect of the invention, standard techniques of molecular biology can be used to prepare nucleic acid molecules encoding synthetic or recombinant polypeptides derived from antibody $V_H$ or $V_L$ domains. Particular nucleotide sequences can be synthesized completely or in part using various oligonucleotide synthesis techniques known in the art, such as site-directed mutagenesis and polymerase chain reaction (PCR) techniques where appropriate. See, e.g., Sambrook, and Maniatis, supra. In particular, one method of obtaining nucleotide sequences encoding the FR and CDR sequences disclosed herein is by annealing of complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) *Proc. Natl. Acad. Sci. USA* 88:4084–4088. Additionally, oligonucleotide directed synthesis (Jones et al. (1986) *Nature* 54:75–82), oligonucleotide directed mutagenesis of preexisting nucleotide regions (Riechmann et al. (1988) *Nature* 332:323–327 and Verhoeyen et al. (1988) *Science* 239:1534–1536), and enzymatic filling in of gapped oligonucleotides using $T_4$ DNA polymerase (Queen et al. (1989) *Proc. Natl. Acad. Sci. USA* 86:10029–10033) can be used under the invention to provide molecules having altered or enhanced antigen-binding capabilities, and/or reduced immunogenicity.

In one particular embodiment of the invention, knowledge of the nucleotide sequences of the $V_H$ and $V_L$ domains of an antibody molecule produced by the 15D3 hybridoma cell line allows for selective optimization of binding affinity in antigen-binding sites produced with those moieties. In this regard, point substitutions can be made in one or more CDRs using conventional cassette mutagenesis or other molecular biology techniques to enhance binding capabilities of an antigen-binding site.

Further, in a related embodiment, entire CDRs may be selectively shuttled into and out of a $V_H$ or $V_L$ coding sequence using recombinant methods known in the art. More particularly, the presence of restriction sites in regions flanking the CDRs makes it possible to cleave one or more CDRs from a molecule. Such restriction sites may in some cases be found in the native coding sequence. Alternatively, recombinant techniques can be used to engineer unique restriction sites into the nucleotide sequences resulting in a synthetic gene which encodes the same V region amino acid sequence due to the degeneracy of the genetic code. Fragments resulting from endonuclease digestion of the V domain nucleotide sequences which comprise the flanking FR-encoding sequences are then ligated to replacement CDR-encoding sequences to provide a synthetic variable domain molecule which displays an altered antigen binding specificity.

Replacement CDR-encoding sequences can be designed empirically under the invention based on sequence analysis of the Fv region of preexisting antibodies. Further, using a computer program such as, for example, COMPUGENE®, and known variable region DNA sequences, those of ordinary skill in the art can design and directly synthesize native or near-native CDR-encoding sequences.

Using transfection and gene delivery techniques as described above, replacement CDR sequences can be readily expressed and the resultant polypeptides tested for binding and empirically refined by exchanging selected amino acids in relatively conserved regions based on observation of trends in amino acid sequence data and/or computer modeling techniques. Thus, significant flexibility in $V_H$ and $V_L$ molecule design is possible under the invention because alterations in amino acid sequences can be made at the DNA level.

Accordingly, in one particular embodiment of the invention, a monomeric $V_H$ domain polypeptide derived from an antibody molecule produced by the 15D3 hybridoma cell line is provided wherein the polypeptide has one CDR selected from the group consisting of HCDR1, HCDR2 and HCDR3. The CDR set in the molecule is completed by two CDRs wherein point substitutions have been introduced into native CDR sequences using conventional cassette mutagenesis, or wherein the CDR comprises a synthetic replacement CDR.

In a related embodiment, a monomeric $V_H$ domain polypeptide derived from an antibody molecule produced by the 15D3 hybridoma cell line is provided wherein the polypeptide has two CDRs selected from the group consisting of HCDR1, HCDR2 and HCDR3. The third CDR comprises either a point substituted native CDR sequence or a synthetic CDR.

In another particular embodiment of the invention, a monomeric $V_L$ domain polypeptide derived from an antibody molecule produced by the 15D3 hybridoma cell line is provided wherein the polypeptide has one CDR selected from the group consisting of LCDR1, LCDR2 and LCDR3. The CDR set in the molecule is completed by two CDRs wherein point substitutions have been introduced into native CDR sequences using conventional cassette mutagenesis, or wherein the CDR comprises a synthetic replacement CDR.

In a related embodiment, a monomeric $V_L$ domain polypeptide derived from an antibody molecule produced by the 15D3 hybridoma cell line is provided wherein the polypeptide has two CDRs selected from the group consisting of LCDR1, LCDR2 and LCDR3. The third CDR comprises either a point substituted native CDR sequence or a synthetic CDR.

In another aspect of the invention, an isolated nucleic acid molecule is provided which comprises a nucleotide sequence encoding a single molecular recognition unit. More particularly, the nucleotide sequence encodes an amino acid sequence that is homologous to a CDR derived from a $V_H$ or $V_L$ domain of an antibody molecule capable of binding specifically to a human tumor cell displaying a MDR phenotype. In a particular embodiment, the molecular recognition unit is homologous to a CDR selected from the $V_H$ or $V_L$ domain of an antibody molecule produced by the 15D3 hybridoma cell line. Thus, the molecular recognition unit is encoded by a nucleotide sequence homologous to a CDR-encoding sequence selected from the group consisting of HCDR1, HCDR2, HCDR3, LCDR1, LCDR2 and LCDR3, SEQ ID NOs: .

The isolated nucleic acid molecule therefore consists essentially of a single coding sequence for the selected CDR; however, the molecule may also include some additional bases or moieties which do not deleteriously affect the basic characteristics of the CDR such as, but not limited to, flanking nucleotide sequences comprising unique restriction sites to enable ligation of nucleotides encoding the subject molecular recognition units into an appropriate site of an antibody variable domain-encoding molecule using recombinant techniques known in the art.

In further related embodiments of the invention, nucleic acid molecules are provided which comprise a plurality of nucleotide sequences, each encoding a molecular recognition unit comprising an amino acid sequence homologous to a CDR derived from a $V_H$ or $V_1$ domain of an antibody molecule capable of binding specifically to a human tumor cell displaying a MDR phenotype. In one embodiment, each molecular recognition unit is homologous to a CDR selected from the $V_H$ or $V_L$ domain of an antibody molecule produced by the 15D3 hybridoma cell line. Thus, the nucleic acid molecules comprise a plurality of molecular recognition unit-encoding sequences homologous to CDR-encoding sequences selected from the group consisting of HCDR1, HCDR2, HCDR3, LCDR1, LCDR2 and LCDR3, SEQ ID NOs: .

In yet a further aspect of the invention, knowledge of the nucleotide sequences of the $V_H$ and $V_L$ domains of an antibody molecule produced by the 15D3 hybridoma cell line allows for the construction of synthetic nucleic acid molecules comprising nucleotide sequences which encode CDRs flanked by recombinantly engineered polypeptide regions. In one embodiment, a nucleic acid molecule is provided which includes nucleotide sequences encoding either a heavy or light chain V domain having a CDR set derived from the $V_H$ or $V_L$ domain, respectively, of an antibody molecule produced by the 15D3 hybridoma cell line. The encoded CDRs are flanked by FRs derived from a heavy or light chain, respectively, of a human immunoglobulin. The resultant xenogeneic chimeric molecule displays immunological binding characteristics imparted by the murine 15D3 antibody-derived CDRs, but has reduced immunogenicity in humans due to the human antibody-derived FRs. See, e.g., Riechmann et al. (1988) *Nature* 332:323–327; Verhoeyen et al. (1988) *Science* 239:1534–1536; and Jones et al. (1986) *Nature* 321:522–525.

Thus, under the invention, the coexpression of two nucleic acid molecules in a suitable host cell; where the first molecule includes nucleotide sequences encoding a CDR set derived from the $V_H$ domain of an antibody molecule produced by the 15D3 hybridoma cell line, wherein the encoded CDRs are flanked by FRs derived from a heavy chain of a human immunoglobulin, and the second molecule includes nucleotide sequences encoding a CDR set derived from the $V_L$ domain of an antibody molecule produced by the 15D3 hybridoma cell line, wherein the encoded CDRs are flanked by FRs derived from a light chain of a human immunoglobulin; provides a convenient method of producing a heterodimeric polypeptide having an antigen-binding site which binds specifically to a human tumor cell displaying a MDR phenotype and which is weakly-immunogenic or non-immunogenic in a human recipient.

In a further related embodiment, a nucleic acid molecule is provided which comprises a nucleotide sequence encoding a CDR selected from the group consisting of HCDR1, HCDR2, HCDR3, LCDR1, LCDR2 and LCDR3, wherein the CDR sequence is interposed by first and second flanking nucleotide sequences. In a particular embodiment, the flanking nucleotide sequences encode FRs derived from murine or human antibody heavy or light chain variable domains. Also provided herein are nucleic acid molecules which comprise a plurality of CDR-encoding sequences selected from the group consisting of HCDR1, HCDR2, HCDR3, LCDR1, LCDR2 and LCDR3, SEQ ID NOs: , wherein the CDRs are interposed by flanking nucleotide sequences derived from murine or human antibody $V_H$ and $V_L$ domains.

Each of the above-described synthetic DNAs are used under the invention to facilitate the empirical refinement of recombinant amino acid sequences encoded by combinations of those nucleic acid molecules to provide synthetic molecules having particularly desired antigen-binding properties. The recombined nucleic acid molecules can be expressed directly in an appropriate host cell, or can be further engineered before expression by the exchange of CDR, FR and FR:CDR:FR sequences with new sequences. CDR and/or FR exchange manipulations are facilitated by PCR techniques (e.g., overlap methods) well known in the art. Such methods generally entail the synthesis of staggered overlapping oligomers including CDR and/or FR sequences derived from both heavy and light chain variable domains using known techniques. The subject oligomers are annealed, ligated and then subjected to PCR amplification using terminal sequences as primers. See, e.g., Jayaraman et al. (1991) *Proc. Natl. Acad. Sci. USA* 88:4084–4088. Other exchange methods are facilitated by the presence of restriction sites which can be engineered into the subject nucleic acid molecules at the FR-CDR and CDR-FR borders.

In yet another aspect of the invention, standard techniques of molecular biology can be used to prepare nucleic acid molecules encoding synthetic or recombinant polypeptides derived from antibody $V_H$ or $V_L$ domains wherein the molecules comprise murine CDRs interposed by flanking recombinantly veneered FR polypeptide regions. The veneering process used herein has been described in the art (see, European Patent Publication No. 519,596, published 23 Dec. 1992, and International Publication No. WO 92/22653, published 23 Dec. 1992, incorporated herein by reference in their entireties).

In one particular embodiment, a synthetic nucleic acid molecule is provided including nucleotide sequences encoding a CDR set derived from the $V_H$ domain of an antibody molecule produced by the 15D3 hybridoma cell line, wherein the CDRs are flanked by recombinantly veneered FR sequences derived from the $V_H$ domain of the same antibody molecule. Thus, the molecule includes three CDR sequences comprising HCDR1, HCDR2 and HCDR3 (SEQ ID NOs: ), that encode CDRs which are supported relative to each other to form an antigen-binding region by flanking veneered FRs.

In a related embodiment, a synthetic nucleic acid molecule is provided including nucleotide sequences encoding a CDR set derived from the $V_L$ domain of an antibody molecule produced by the 15D3 hybridoma cell line, wherein the CDRs are flanked by recombinantly veneered FRs derived from the $V_L$ domain of the same antibody molecule. Thus, the molecule includes three CDR sequences comprising LCDR1, LCDR2 and LCDR3 (SEQ ID NOs: ), that encode CDRs which are supported relative to each other to form an antigen-binding region by flanking veneered FRs.

The veneering method used herein to provide the above-described synthetic molecules includes the following steps. Initially, the FR sequences derived from the $V_H$ and $V_L$ domains of a 15D3 antibody molecule are compared with corresponding FR sequences of human variable domains obtained from an appropriate database. See, e.g., Kabat et al., in *Sequences of Proteins of Immunological Interest*, 4th ed., (U.S. Dept. of Health and Human Services, U.S. Government Printing Office, 1987). Human frameworks with a high degree of sequence similarity to those of the murine 15D3 regions are identified. Sequence similarity is measured using identical residues as well as evolutionarily conservative amino acid substitutions. Similarity searches are performed using the 15D3 framework sequence from which the CDRs have been removed. The framework sequence is used to query a database of human immunoglobulin sequences derived from multiple sources. Sequences with a high degree of sequence similarity are examined individually for their potential as humanizing framework sequences. In this way, the human homologue providing the 15D3 CDRs with the structure most similar to their native murine framework is selected as the template for the construction of the veneered FRs.

The selected human V regions are then compared residue by residue to the corresponding 15D3 amino acids. The residues in the murine FRs which differ from the selected human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" FRs are designed to retain the 15D3 CDR residues, the residues substantially adjacent to the CDRs, the residues identified as buried or mostly buried (solvent inaccessible), the residues believed to participate in non-covalent (e.g., electrostatic) interchain contacts, and the residues from conserved structural regions of the FRs which are believed to influence the "canonical" tertiary structures of the CDR loops.

Accordingly, recombinant nucleotide sequences which combine CDRs derived from an antibody molecule produced by the 15D3 hybridoma cell line with the human-appearing veneered FRs can be introduced into suitable host cells for the expression of recombinant human antibodies which exhibit the antigen specificity of the murine antibody molecule. More particularly, expression cassettes, comprising polynucleotide sequences encoding the subject recombinant molecules—operably linked to a control sequence that is capable of directing the expression thereof—can be introduced into a suitable host cell for expression using standard gene transfer protocols. The subject polypeptides can thus be expressed in appropriate prokaryotic or eukaryotic hosts as described above. Additionally, coexpression of complementary $V_H$ and $V_L$ molecules having veneered frameworks provides a convenient method of producing a heterodimeric polypeptide featuring an antigen-binding site which binds specifically to a human tumor cell displaying a MDR phenotype and which is weakly-immunogenic, or substantially non-immunogenic in a human recipient.

Each of the synthetic molecules described herein may be expressed using a monovalent phage display system as described by Garrad et al. (1991) *Biotechnology* 9:1373–1377, to identify $V_H/V_L$ pairs with a desired specificity or to modify the specificity or affinity of a given $V_H/V_L$ pair. In this regard, improvement of antigen binding affinity of a given $V_H/V_L$ pair can be accomplished by constructing phage libraries—in which at least one CDR comprises a synthetic or point mutated CDR—and screening the phage system for molecules which exhibit enhanced binding characteristics or lower off rates using ligand affinity analysis methods well known in the art. Additionally, a phage display system can be used under the invention to facilitate "chain shuffling" in which a given $V_H$ or $V_L$ is re-paired with a library of random $V_L$ or $V_H$ sequences and the resulting phage screened for desired antigen binding behavior. Suitable phage display systems have been described (McCafferty et al. (1990) *Nature* 348:552–554), and chain shuffling techniques are known in the art. See, e.g., Figini et al. (1994) *J. Mol. Biol.* 239:68–78.

In another aspect of the invention, biosynthetic single-chain Fv (sFv) molecules are provided. The sFv polypeptides are termed "biosynthetic" in the sense that they are synthesized and re-cloned in a cellular host made to express a protein encoded by a plasmid which includes a coding sequence based in part on synthetic DNA, that is, a recombinant DNA made from ligation of plural, chemically synthesized and re-cloned oligonucleotides, or by ligation of fragments of DNA derived from the genome of 15D3 hybridomas. The sFv molecules are properly characterized as "antibody binding sites" in that the synthetic single polypeptide chains are able to refold into a 3-dimensional conformation designed specifically to have affinity for human cancer cells displaying a MDR phenotype or related tumor antigens. The inventive sFv molecules are produced herein using methods described in the art. See, e.g., Huston et al. (1988) *Proc. Nat. Acad. Sci. USA* 85(16):5879–5883; U.S. Pat. Nos. 5,091,513 and 5,132,405, to Huston et al.; and U.S. Pat. No. 4,946,778, to Ladner et al.

In one particular embodiment, an sFv molecule is provided wherein the CDRs and FRs are derived from an antibody molecule capable of binding specifically to a human tumor cell expressing a MDR phenotype. The subject sFv polypeptide includes a series of residues consisting of amino acids defining at least three polypeptide segments which together form the tertiary molecular structure responsible for affinity and binding. The CDRs are held in appropriate conformation by polypeptide segments analogous to the FRs of a Fv fragment derived from a native antibody molecule.

More particularly, an isolated nucleic acid molecule is provided having a nucleotide sequence encoding a sFv polypeptide that exhibits antibody-binding specificity of an antibody capable of binding to a human tumor cell displaying a MDR phenotype. The sFv molecule comprises first, second and third domains; wherein the first polypeptide domain has an amino acid sequence that is homologous to a $V_H$ domain of an antibody molecule, the second polypeptide domain has an amino acid sequence that is homologous to a $V_L$ domain of an antibody molecule, and the third polypeptide domain comprises an amino acid sequence spanning the distance between the C-terminus of one of the first or second domains and the N-terminus of the other to provide a single chain polypeptide.

In one particular embodiment, the sFv molecule comprises a first polypeptide domain that comprises an amino acid sequence homologous to the $V_H$ domain of an antibody produced by the 15D3 hybridoma cell line, and the second polypeptide domain comprises an amino acid sequence that is homologous to the $V_L$ domain of a 15D3 antibody. The first and second polypeptide domains are linked together by a polypeptide linker that is not necessarily derived from an antibody molecule.

Under the invention, recombinant design methods can be used to develop suitable chemical structures (linkers) for converting two naturally associated—but chemically separate—heavy and light polypeptide chains from an antibody variable region into a sFv molecule which will fold into a three-dimensional structure that is substantially similar to native antibody structure. Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$ and $V_L$ chains. Thus, suitable linkers under the invention generally comprise polypeptide chains of alternating sets of glycine and serine residues, and may include glutamic acid and lysine residues inserted to enhance solubility. One particular linker under the invention has the amino acid sequence [(Gly)$_4$Ser]$_3$. Another particularly preferred linker has the amino acid sequence comprising 2 or 3 repeats of [(Ser)$_4$Gly], such as [(Ser)$_4$Gly]$_3$. Nucleotide sequences encoding such linker moieties can be readily provided using various oligonucleotide synthesis techniques known in the art. See, e.g., Sambrook, and Maniatis, supra.

In further related embodiments, nucleic acid molecules encoding various synthetic antibody variable domain moieties can be combined to provide sFv molecules comprising murine CDRs supported by human frameworks, antigen-binding sites having recombinantly veneered heavy and light chain FRs, and re-paired CDRs and/or CDR sets as described above. Accordingly, the construction of nucleic acid molecules including nucleotide sequences encoding the single-chain Fv and sFv fusion molecules of the invention can be practiced using known techniques. Such methods include the use of various restriction enzymes which make sequence-specific cuts in DNA to produce blunt ends or cohesive ends, DNA ligases, techniques enabling enzymatic addition of sticky ends to blunt-ended DNA, construction of synthetic polynucleotides by assembly of short or medium length oligonucleotides, cDNA synthesis techniques, and synthetic probes for isolating immunoglobulin genes.

In particular, one method of obtaining nucleotide sequences encoding the sFv molecules disclosed herein is by an overlap PCR approach. See, e.g., Horton et al. (1990) *BioTechniques* 8:528–535. The ends of the light and heavy chain variable regions that are to be joined through a linker sequence are first extended by PCR amplification of each variable region, using primers that contain the terminal sequence of the variable region followed by all or most of the desired linker sequence. After this extension step, the light and heavy chain variable regions contain overlapping extensions which jointly contain the entire linker sequence, and which can be annealed at the overlap and extended by PCR to obtain the complete sFv sequence using methods known in the art.

Practice of the invention enables the design and biosynthesis of a wide variety of molecules, all of which are characterized by a region having affinity for a tumor cell displaying the MDR phenotype. Additional regions of the biosynthetic proteins are designed with the particular planned utility of the molecule in mind. Thus, if the molecule is designed for intravascular use in mammals, the FRs may include amino acid sequences that are similar, or identical to at least a portion of immunoglobulin FRs native to that mammalian species.

More particularly, the invention includes the use of sFv molecules and humanized sFv binding sites in diagnostic imaging methods and tumor therapies. The subject molecules can be administered by intravenous or intramuscular injection. Effective dosages for the sFv constructs in anti-tumor therapies or in effective tumor imaging can be determined by routine experimentation, keeping in mind the objective of the treatment.

Pharmaceutical forms suitable for injectable use include sterile aqueous solutions or dispersions. In all cases, the form must be sterile and must be fluid so as to be easily administered by syringe. The sFv molecules must further be stable under the conditions of manufacture and storage, and must be preserved against the contaminating action of microorganisms. This may, for example, be achieved by filtration through a sterile 0.22 micron filter and/or lyophilization followed by sterilization with a gamma ray source.

Sterile injectable solutions are prepared by incorporating the single chain polypeptide constructs of the invention in the required amount in the appropriate solvent, such as sodium phosphate-buffered saline, followed by filter sterilization. As used herein, "a physiologically acceptable carrier" includes any and all solvents, dispersion media, antibacterial and antifungal agents that are non-toxic to humans, and the like. The use of such media and agents for pharmaceutically active substances is well known in the art. The media or agent must be compatible with maintenance of proper conformation of the single polypeptide chains, and its use in the therapeutic compositions. Supplementary active ingredients can also be incorporated into the compositions.

The above-described biosynthetic sFv molecules having affinity for a tumor cell displaying a MDR phenotype can be used to develop retroviral vectors that target human cancer cells expressing the MDR phenotype, and are thus useful in the design and development of gene therapy strategies. In this regard, mammalian retrovirus vectors commonly used for gene transfer are capable of infecting a host range determined primarily by the binding interaction between viral envelope glycoproteins and specific proteins on the host cell surface that act as viral receptors. Varmus, H. (1988) *Science* 240:1427; and Weiss et al., eds., *RNA Tumor Viruses: Molecular Biology of Tumor Viruses* (Cold Spring Harbor Laboratory, Cold Spring Harbor, N.Y., 1984). It has been demonstrated that the host range of viruses can be altered by pseudotyping, using alternative envelope proteins derived from naturally occurring viral sequences such as those of the avian leukosis virus and the human immunodeficiency virus. Wilson et al. (1989) *J. Virol.* 63:2374. Recently, the polypeptide hormone erythropoietin (EPO) has been introduced into the ecotropic Moloney murine leukemia virus (Mo-MuLV) envelope. Kasahara et al. (1994) *Science* 266:1373. The resultant murine virus became several times more infectious for murine cells bearing the EPO receptor, and also became infectious for human cells bearing the EPO receptor, indicating that tissue-specific targeting using recombinantly engineered viral envelopes has broad application in a variety of gene delivery systems.

A recombinant virus containing in its envelope a sequence encoding a sFv molecule including an antigen-binding site has been shown to bind to a solid matrix containing the appropriate polypeptide antigen, and the bound viruses were infectious for NIH 3T3 cells. Russell et al. (1993) *Nucl. Acids Res.* 21:1081. Thus, in one embodiment of the invention, the nucleic acid molecules provided under the invention can be recombinantly engineered into various retroviral systems (U.S. Pat. No. 5,219,740; Miller and Rosman (1989) *BioTechniques* 7:980–990; Miller, A. D. (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Cur. Opin. Genet. Develop.* 3:102–109), using recombinant techniques known in the art. The nucleic acid molecules of the invention can also be engineered into a suitable adenovirus vector, such as those which have been described in the art. (Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner, K. L. (1988) *BioTechniques* 6:616–629; and Rich et al. (1993) *Human Gene Therapy* 4:461–476). The methods generally entail removal of a portion of a viral envelope gene and replacement, in frame, with nucleotide sequences encoding the polypeptides of the invention. The constructs can be cotransfected into appropriate packaging cells, and transfected cells selected and screened using known techniques. Cells containing correctly oriented chimeric envelope proteins can then be selected and isolated, and virus-producing cell lines generated by infection of packaging cells with virion-containing cell culture medium harvested after transient transfection with wild-type packaging cells using known techniques. See, e.g., Miller et al. (1986) *Molec. Cell. Biol.* 6:2895; Bender et al. (1987) *J. Virol.* 61:1639; Eglitis et al. (1988) *BioTechniques* 6:608; and Mann et al. (1983) *Cell* 33:153.

The single chain polypeptide motif of sFv molecules formed under the invention provides a convenient means for designing multi-functional molecules such as immunotoxins and the like. In this regard, additional nucleotide sequences encoding, for example, antibody constant region fragments can be linked to sFv coding sequences to provide a bifunctional molecule. The single polypeptide chains of the invention may also include ancillary polypeptide regions defining a leader sequence or a second polypeptide chain that is bioactive such as a cytokine, toxin, ligand, hormone, or enzyme, or a site onto which a toxin, drug, or a remotely detectable moiety can be attached.

Thus, in a further aspect of the invention, a nucleic acid molecule is provided that encodes a sFv polypeptide comprising a third polypeptide domain. The third polypeptide domain is joined to either the first or second polypeptide domain by a second polypeptide linker moiety spanning the distance between the C-terminus or N-terminus of one of the first or second domains, and the N-terminus or C-terminus, respectively, of the third polypeptide domain.

In one embodiment, the third polypeptide domain comprises a second antigen-binding site. The second antigen-binding site is formed from a first portion derived from a $V_H$ domain of an antibody, a second portion derived from a $V_L$ domain of an antibody and a third portion comprising a polypeptide linker spanning the distance between the C-terminus of one of the first or second portions and the N-terminus of the other, whereby the linker joins the first and second portions to define a second antigen-binding site which is capable of immunological binding activity. In one embodiment, the CDRs in the first and second portions of the third polypeptide domain are derived from an antibody produced by the 15D3 hybridoma cell line.

In another embodiment, the third polypeptide domain comprises at least a portion of a human or murine antibody Fc polypeptide. More particularly, a sFv-encoding nucleic acid molecule is provided under the invention wherein an attached nucleotide sequence encodes an ancillary amino acid sequence homologous to an Fc polypeptide fragment such as an IgG fragment, whereby the third polypeptide region is capable of binding IgG-isotype specific Fc receptors. In one particular embodiment, the third polypeptide-encoding sequence encodes a Fc fragment derived from a human IgG molecule, or a peptide sequence substantially homologous thereto.

In a related embodiment, a sFv molecule is provided wherein the molecule is fused to a third polypeptide domain comprising an amino acid sequence derived from the transmembrane and cytoplasmic domain of the ζ chain of the T-cell receptor CD3 complex. More particularly, a chimeric nucleic acid molecule is provided which includes a nucleotide sequence encoding a sFv molecule as described above fused to a nucleotide sequence encoding a polypeptide which is substantially homologous to the ζ chain of the CD3 complex. See e.g., U.S. Pat. No. 5,359,046. In this regard, it has been shown that the cytoplasmic tail of the ζ chain can activate T cells independently of the rest of the receptor complex. Letourneur et al. (1992) *Science* 255: 79–82. Thus, in one embodiment, a nucleic acid molecule is provided comprising a nucleotide sequence encoding a sFv molecule, said sFv molecule having first and second polypeptide domains derived from the $V_H$ and $V_L$ domain, respectively, of an antibody produced by the 15D3 hybridoma cell line, wherein the sFv-encoding sequence is fused to a nucleotide sequence encoding a polypeptide hinge region which, in turn, is fused to a nucleotide sequence encoding a polypeptide derived from the ζ chain of a T-cell receptor complex using methods described in the art. See e.g., Moritz, et al. (1994) *Proc. Natl. Acad. Sci. USA* 91:4318–4322. The subject chimera confers a MDR phenotype antigen-specific immunological binding function on the ζ chain of the T cell receptor complex, thereby circumventing major histocompatibility complex (MHC)-restricted antigen recognition. The subject nucleic acid molecule can be transferred into cytotoxic T-cells using retroviral and other gene transfer techniques as described above.

In yet a further embodiment, the third polypeptide domain comprises an amino acid sequence capable of covalently or non-covalently associating with a detectable moiety. In this regard, the third polypeptide domain can be designed to enable the attachment of a detectable moiety such as, but not limited to, radioactive isotopes, fluorescers, chemiluminescers, enzymes, enzyme substrates, enzyme cofactors, enzyme inhibitors, dyes, and metal ions using chemical attachment techniques known in the art.

In one particular embodiment, the third polypeptide domain includes a site which can be labelled with radioisotopes such as Iodine-131, Indium-111, and Technetium-99m, for example. Beta emitters such as Technetium-99m and Indium-111 are preferred because they are detectable with a gamma camera and have favorable half-lives for imagining in vivo. The single polypeptide chains can be labelled, for example, with radioactive atoms such as, but not limited to, Yttrium-90, Technetium-99m, or Indium-111 via a conjugated metal chelator (see, e.g., Khaw et al. (1980) *Science* 209:295; U.S. Pat. No. 4,472,509 to Gansow et al.; and U.S. Pat. No. 4,479,930 to Hnatowich), or by other standard means of isotope linkage to proteins known to those with skill in the art.

In another embodiment of the invention, the third polypeptide domain can be designed to include a site capable of attaching a chemotherapeutic agent using immunoconjugate techniques well known in the art. In this regard, conjugation of a number of chemotherapeutic agents to immunoglobulin molecules have been described, including doxorubicin (Yang et al. (1988) *Proc. Natl. Acad. Sci. USA* 85:1189–1193), daunorubicin (Diener et al. (1985) *Science* 231:148–150; Dillman et al. (1988) *Cancer Res.* 48:6097–6102), methotrexate (Uadia et al. (1985) *J Natl Cancer Inst.* 74:29–35; Deguchi et al. (1986) *Cancer Res.* 46:3751–3755), and chlorambucil (Symth et al. (1986) *J Immunol.* 137:3361–3366).

In yet a further related embodiment, the third polypeptide domain comprises an amino acid sequence capable of attaching to, or comprising a toxin such as ricin, abrin, diphtheria toxin and Pseudomonas exotoxin, or an enzymatically active portion (A chains) thereof. See, e.g., U.S. Pat. No. 4,753,894 to Frankel et al.; Nevelle, et al. (1982) *Immunol Rev* 62:75–91; Ross et al. (1980) *European J Biochem* 104; Vitteta et al. (1982) *Immunol Rev* 62:158–183; Raso et al. (1982) *Cancer Res* 42:457–464, and Trowbridge et al. (1981) *Nature* 294:171–173.

Thus, in one particular embodiment, a toxin is attached to the sFv-encoding nucleic acid molecule using methods known in the art. More particularly the toxin comprises ricin, an enzyme from the castor bean that is highly toxic, or a portion of ricin that confers toxicity. At concentrations as low as 1 ng/ml ricin efficiently inhibits the growth of cells in culture. The ricin A chain has a molecular weight of about 30,000 and is glycosylated. The ricin B chain has a larger size (about 34,000 molecular weight) and is also glycosylated. The B chain contains two galactose binding sites, one in each of the two domains in the folded subunit. The crystallographic structure for ricin shows the backbone tracing of the A chain. There is a cleft, which is probably the active site, that runs diagonally across the molecule. Also present is a mixture of α-helix, β-structure, and irregular structure in the molecule.

The A chain enzymatically inactivates the 60S ribosomal subunit of eukaryotic ribosomes. The B chain binds to galactose-based carbohydrate residues on the surfaces of cells. It appears to be necessary to bind the toxin to the cell surface, and also facilitates and participates in the mechanics of entry of the toxin into the cell. Because all cells have galactose-containing cell surface receptors, ricin inhibits all types of mammalian cells with nearly the same efficiency.

Ricin A chain and ricin B chain are encoded by a gene that specifies both the A and B chains. The polypeptide synthesized from the mRNA transcribed from the gene contains A chain sequences linked to B chain sequences by a 'J' (for joining) peptide. The J peptide fragment is removed by post-translational modification to release the A and B chains. However, A and B chains are still held together by the interchain disulfide bond. The preferred form of ricin is recombinant A chain as it is totally free of B chain and, when expressed in *E. coli,* is unglycosylated and thus cleared from the blood more slowly than the glycosylated form. The specific activity of the recombinant ricin A chain against ribosomes and that of native A chain isolated from castor bean ricin are equivalent. The nucleotide sequence and corresponding amino acid sequence of ricin A chain are known in the art. Roberts et al. (1992) *Targeted Diagn. Therap.* 7:81–97.

Recombinant ricin A chain, plant-derived ricin A chain, deglycosylated ricin A chain, or derivatives thereof, can be targeted to a human cancer cell displaying a MDR phenotype by the sFv polypeptide of the present invention. To do this, the third polypeptide domain of the sFv molecule can be chemically crosslinked to the ricin A chain form of choice. In one particular embodiment a single-chain Fv-ricin A chain immunotoxin can be formed by fusing the single-chain Fv polypeptide to one or more ricin A chains through the corresponding gene fusion. By replacing the B chain of ricin with an antigen-binding site specific to the P-glycoprotein antigen, the A chain is guided to such antigens on the tumor cell surface. In this way the selective killing of tumor cells expressing these antigens can be achieved. Such target cell selectivity has been demonstrated in many cases against cells grown in culture and generally depends on the presence or absence of antigens on the surface of the cells to which the immunotoxin is directed.

In yet another aspect of the invention, expression cassettes, comprising polynucleotide sequences encoding the sFv polypeptide molecules operably linked to a control sequence that is capable of directing the expression of sFv molecules (and sFv molecules with ancillary polypeptide regions), can be introduced into a suitable host cell for expression using standard gene transfer protocols. The subject polypeptides can thus be expressed in appropriate prokaryotic hosts such as various strains of *E. coli,* and in eukaryotic hosts such as Chinese hamster ovary cells (CHO), mouse myeloma, hybridoma, transfectoma, and human myeloma cells.

More particularly, the sFv molecules can be expressed in *E. coli.* The nucleic acid molecule encoding a sFv molecule of interest is first cloned into an expression vector. This can be accomplished by positioning the engineered polynucleotide sequence downstream from a promoter sequence such as Trp or Tac, and a nucleotide sequence coding for a leader polypeptide such as fragment B (FB) of staphylococcal protein A. The resulting expressed fusion protein accumulates in refractile bodies in the cytoplasm of the cells, and may be harvested after disruption of the cells by French press or sonication. The refractile bodies are solubilized, and the expressed fusion molecules are cleaved and refolded by the methods already established for many other recombinant proteins (Huston et al. (1988) *Proc. Natl. Acad. Sci. USA* 85:5879) or, for direct expression methods, there is no leader and the inclusion bodies may be refolded without cleavage (Huston et al. (1991) *Methods in Enzymology* 203:46–88).

Further under the invention, subsequent proteolytic cleavage of the isolated sFv from its leader sequence fusions can be performed to yield free sFvs, which can be renatured to obtain an intact biosynthetic, hybrid antigen-binding site. The cleavage site preferably is immediately adjacent to the sFv polypeptide and includes one amino acid or a sequence of amino acids exclusive of any one amino acid or amino acid sequence found in the amino acid structure of the single polypeptide chain.

The cleavage site preferably is designed for specific cleavage by a selected agent. Endopeptidases are preferred, although non-enzymatic (chemical) cleavage agents can be used. Many useful cleavage agents, for instance, cyanogen bromide, dilute acid, trypsin, *Staphylococcus aureus* V-8 protease, post-proline cleaving enzyme, blood coagulation Factor Xa, enterokinase, andrenin, recognize and preferentially or exclusively cleave at particular cleavage sites. One particularly preferred peptide sequence cleavage agent is V-8 protease, and the preferred cleavage site is at a Glu residue. Other useful enzymes recognize multiple residues as a cleavage site, e.g., factor Xa (which recognizes a four amino acid sequence of Ile, Glu, Gly and Arg residues, respectively), or enterokinase (which recognizes a five amino acid sequence having four Asp residues, and one Lys residue, respectively). Dilute acid preferentially leaves the peptide bond between Asp-Pro residues, and CNBr in acid cleaves after Met, unless it is followed by Tyr.

In a related embodiment, the subject sFv molecules can be expressed in eukaryotic hybridoma cells. The nucleic acid molecule is first inserted into an expression vector containing, for example, the immunoglobulin promoter, a secretion signal, immunoglobulin enhancers, and various introns. The resultant vector can also contain sequences encoding an ancillary polypeptide such as described above. The vector is then transfected into myeloma cells via established electroporation or protoplast fusion methods. Transfected host cells thus express $V_H$-linker-$V_L$ or $V_L$-linker-$V_H$ sFv polypeptides, each of which may be attached in the various ways discussed above to a protein domain having another function (e.g., cytotoxicity).

It is to be understood that while the invention has been described in conjunction with specific embodiments thereof, that the description above is intended to illustrate and not limit the scope of the invention. Other aspects, advantages and modifications within the scope of the invention will be apparent to those skilled in the art to which the invention pertains.

Deposits of Strains Useful in Practicing the Invention

A deposit of biologically pure cultures of the following strains was made with the American Type Culture Collection (ATCC), 12301 Parklawn Drive, Rockville, Md. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit and at least five (5) years after the most recent request for the furnishing of a sample of the deposit by the depository. The organisms will be made available by the ATCC under the terms of the Budapest Treaty, which assures permanent and unrestricted availability of the cultures to one determined by the U.S. Commissioner of Patents and Trademarks to be entitled thereto according to 35 USC §122 and the Commissioner's rules pursuant thereto (including 37 CFR §1.12).

These deposits are provided merely as convenience to those of skill in the art, and are not an admission that a deposit is required under 35 USC §112. The nucleic acid sequences of these hybridomas, as well as the amino acid sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|--------|--------------|----------|
| 15D3   | May 6, 1993  | HB11342  |

I claim:

1. A monomeric polypeptide that binds to a human tumor cell displaying a multiple-drug resistance, said monomeric polypeptide comprising:

a) a polypeptide domain which includes amino acid sequences comprising HCDR1 (residues 31–35 of SEQ ID NO:16), HCDR2 (residues 50–66 of SEQ ID NO:16), and HCDR3 (residues 99–108 of SEQ ID NO:16).

2. The monomeric polypeptide of claim 1, wherein said polypeptide domain further comprises heavy chain framework amino acid residues which are selectively replaced with human heavy chain framework amino acid residues to provide a veneered molecule.

3. A monomeric polypeptide that binds to a human tumor cell displaying a multiple-drug resistance, said monomeric polypeptide comprising:

a) a polypeptide domain which includes an amino acid sequence consisting of HCDR3 (residues 99–108 of SEQ ID NO:16).

4. A dimeric polypeptide that binds to a human tumor cell displaying a multiple-drug resistance, said dimeric polypeptide comprising:

a) a first polypeptide domain which includes a first set of amino acid sequences comprising HCDR1 (residues 31–35 of SEQ ID NO:16), HCDR2 (residues 50–66 of SEQ ID NO:16), and HCDR3 (residues 99–108 of SEQ ID NO:16); and b) a second polypeptide domain which includes a second set of amino acid sequences comprising LCDR1 (residues 24–39 of SEQ ID NO:18), LCDR2 (residues 55–61 of SEQ ID NO:18), and LCDR3 (residues 94–102 of SEQ ID NO:18).

5. The dimeric polypeptide of claim 4, wherein the antibody is a monoclonal antibody produced by the hybridoma cell line 15D3 (ATCC No. HB11342).

6. The dimeric polypeptide of claim 4, wherein said first polypeptide domain further comprises heavy chain framework amino acid residues which are selectively replaced with human heavy chain framework amino acid residues to provide a veneered molecule, and said second polypeptide domain further comprises light chain framework amino acid residue which are selectively replaced with human light chain framework amino acid residues to provide a veneered molecule.

7. The dimeric polypeptide of claim 4 further comprising at least one polypeptide linker, wherein said polypeptide linker comprises an amino acid sequence spanning the distance between the C-terminus of one of the first or second polypeptide domains and the N-terminus of the other, thereby joining said first and second polypeptide domains into a single chain polypeptide.

8. The dimeric polypeptide of claim 7, wherein the polypeptide linker is not derived from an antibody molecule.

9. The dimeric polypeptide of claim 4, wherein the first and second polypeptide domains comprise the heavy chain and light chain complementarity-determining regions (CDRs), respectively, of a monoclonal antibody produced by the hybridoma cell line 15D3 (ATCC No. HB11342).

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

A G G T A T A C C A   T G T C T
                                    1 5

( 2 ) INFORMATION FOR SEQ ID NO:2:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ACCATTAGTA GTGGTGGTGG TAACACCTAC TATCCAGACA GTGTGAAGGG T 51

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TACGGGGCTG GTGACGCCTG GTTTGCTTAC 30

( 2 ) INFORMATION FOR SEQ ID NO:4:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GAGGTGAAGG TTGTGGAGTC TGGGGGAGTC TTAGTGAGGC CTGGAGGGTC CCTGAAACTC 60

TCCTGTGCAG CCTCTGGATT CACTTTCAGT 90

( 2 ) INFORMATION FOR SEQ ID NO:5:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TGGGTTCGCC AGACTCCGGA GAAGCGGCTG GAGTGGGTCG CA 42

( 2 ) INFORMATION FOR SEQ ID NO:6:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CGATTCACCG TCTCCAGAGA CAATGCCATG AGCAGCCTGT ACCTGCAAAT GAGCAGTCTG 60

AGGTCTGAGG ACACGGCCTT GTATTACTGT GCAAGA 96

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TGGGGCCAAG GGACTCTGGT CACAGTTTCT GCA 33

( 2 ) INFORMATION FOR SEQ ID NO:8:

( i ) SEQUENCE CHARACTERISTICS:
        ( A ) LENGTH: 48 base pairs
        ( B ) TYPE: nucleic acid (C) STRANDEDNESS: single
(D) TOPOLOGY: linear (xi) SEQUENCE DESCRIPTION: SEQ ID NO:8:

AGATCCAGTC AGAGCATTGT GCATAGTACT GGAAACACCT ATTTAGAG        48

(2) INFORMATION FOR SEQ ID NO:9:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (xi) SEQUENCE DESCRIPTION: SEQ ID NO:9:

AAAGTTTCCA ACCGATTTTC T        21

(2) INFORMATION FOR SEQ ID NO:10:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (xi) SEQUENCE DESCRIPTION: SEQ ID NO:10:

TTTCAAGGTT CACATTTTCC TCGGACG        27

(2) INFORMATION FOR SEQ ID NO:11:

(i) SEQUENCE CHARACTERISTICS:
  (A) LENGTH: 69 base pairs
  (B) TYPE: nucleic acid
  (C) STRANDEDNESS: single
  (D) TOPOLOGY: linear (xi) SEQUENCE DESCRIPTION: SEQ ID NO:11:

GAGCTCGCGA TGACCCAGAC TCCACTCTCC CTGCCTGTCA GTCTTGGAGA TCAAGCCTCC        60

ATCTCTTGC        69

(2) INFORMATION FOR SEQ ID NO:12:

(i) SEQUENCE CHARACTERISTICS:
  (A) LENGTH: 45 base pairs
  (B) TYPE: nucleic acid
  (C) STRANDEDNESS: single
  (D) TOPOLOGY: linear (xi) SEQUENCE DESCRIPTION: SEQ ID NO:12:

TGGTACCTGC AGAAACCAGG CCAGTCTCCA AAGCTCCTGA TCTAC        45

(2) INFORMATION FOR SEQ ID NO:13:

(i) SEQUENCE CHARACTERISTICS:
  (A) LENGTH: 96 base pairs
  (B) TYPE: nucleic acid
  (C) STRANDEDNESS: single
  (D) TOPOLOGY: linear (xi) SEQUENCE DESCRIPTION: SEQ ID NO:13:

GGGGTCCCAG ACAGGTTCAG TGGCAGTGGA TCAGGACAG ATTTCACACT CAAGATCAGT        60

AGACTGGAGG CTGAGGATCT GGGAGTTTAT TACTGC        96

(2) INFORMATION FOR SEQ ID NO:14:

(i) SEQUENCE CHARACTERISTICS:

(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:14:

TTCGGTGGAG GCACCAGGCT GGAAATCAAG                30

(2) INFORMATION FOR SEQ ID NO:15:

(i) SEQUENCE CHARACTERISTICS:
(A) LENGTH: 357 base pairs
(B) TYPE: nucleic acid
(C) STRANDEDNESS: single
(D) TOPOLOGY: linear (ix) FEATURE:
(A) NAME/KEY: CDS
(B) LOCATION: 1..357

(xi) SEQUENCE DESCRIPTION: SEQ ID NO:15:

| GAG | GTG | AAG | GTT | GTG | GAG | TCT | GGG | GGA | GTC | TTA | GTG | AGG | CCT | GGA | GGG | 48 |
|---|---|---|---|---|---|---|---|---|---|---|---|---|---|---|---|---|
| Glu | Val | Lys | Val | Val | Glu | Ser | Gly | Gly | Val | Leu | Val | Arg | Pro | Gly | Gly | |
| 1 | | | | 5 | | | | | 10 | | | | | 15 | | |

| TCC | CTG | AAA | CTC | TCC | TGT | GCA | GCC | TCT | GGA | TTC | ACT | TTC | AGT | AGG | TAT | 96 |
|---|---|---|---|---|---|---|---|---|---|---|---|---|---|---|---|---|
| Ser | Leu | Lys | Leu | Ser | Cys | Ala | Ala | Ser | Gly | Phe | Thr | Phe | Ser | Arg | Tyr | |
| | | | 20 | | | | | 25 | | | | 30 | | | | |

| ACC | ATG | TCT | TGG | GTT | CGC | CAG | ACT | CCG | GAG | AAG | CGG | CTG | GAG | TGG | GTC | 144 |
|---|---|---|---|---|---|---|---|---|---|---|---|---|---|---|---|---|
| Thr | Met | Ser | Trp | Val | Arg | Gln | Thr | Pro | Glu | Lys | Arg | Leu | Glu | Trp | Val | |
| | | 35 | | | | | 40 | | | | | 45 | | | | |

| GCA | ACC | ATT | AGT | AGT | GGT | GGT | GGT | AAC | ACC | TAC | TAT | CCA | GAC | AGT | GTG | 192 |
|---|---|---|---|---|---|---|---|---|---|---|---|---|---|---|---|---|
| Ala | Thr | Ile | Ser | Ser | Gly | Gly | Gly | Asn | Thr | Tyr | Tyr | Pro | Asp | Ser | Val | |
| | | 50 | | | | 55 | | | | | 60 | | | | | |

| AAG | GGT | CGA | TTC | ACC | GTC | TCC | AGA | GAC | AAT | GCC | ATG | AGC | AGC | CTG | TAC | 240 |
|---|---|---|---|---|---|---|---|---|---|---|---|---|---|---|---|---|
| Lys | Gly | Arg | Phe | Thr | Val | Ser | Arg | Asp | Asn | Ala | Met | Ser | Ser | Leu | Tyr | |
| 65 | | | | | 70 | | | | | 75 | | | | | 80 | |

| CTG | CAA | ATG | AGC | AGT | CTG | AGG | TCT | GAG | GAC | ACG | GCC | TTG | TAT | TAC | TGT | 288 |
|---|---|---|---|---|---|---|---|---|---|---|---|---|---|---|---|---|
| Leu | Gln | Met | Ser | Ser | Leu | Arg | Ser | Glu | Asp | Thr | Ala | Leu | Tyr | Tyr | Cys | |
| | | | | 85 | | | | | 90 | | | | | 95 | | |

| GCA | AGA | TAC | GGG | GCT | GGT | GAC | GCC | TGG | TTT | GCT | TAC | TGG | GGC | CAA | GGG | 336 |
|---|---|---|---|---|---|---|---|---|---|---|---|---|---|---|---|---|
| Ala | Arg | Tyr | Gly | Ala | Gly | Asp | Ala | Trp | Phe | Ala | Tyr | Trp | Gly | Gln | Gly | |
| | | | 100 | | | | | 105 | | | | | 110 | | | |

| ACT | CTG | GTC | ACA | GTT | TCT | GCA | | | | | | | | | | 357 |
|---|---|---|---|---|---|---|---|---|---|---|---|---|---|---|---|---|
| Thr | Leu | Val | Thr | Val | Ser | Ala | | | | | | | | | | |
| | | | 115 | | | | | | | | | | | | | |

(2) INFORMATION FOR SEQ ID NO:16:

(i) SEQUENCE CHARACTERISTICS:
(A) LENGTH: 119 amino acids
(B) TYPE: amino acid
(D) TOPOLOGY: linear (ii) MOLECULE TYPE: protein (xi) SEQUENCE DESCRIPTION: SEQ ID NO:16:

| Glu | Val | Lys | Val | Val | Glu | Ser | Gly | Gly | Val | Leu | Val | Arg | Pro | Gly | Gly |
|---|---|---|---|---|---|---|---|---|---|---|---|---|---|---|---|
| 1 | | | | 5 | | | | | 10 | | | | | 15 | |

| Ser | Leu | Lys | Leu | Ser | Cys | Ala | Ala | Ser | Gly | Phe | Thr | Phe | Ser | Arg | Tyr |
|---|---|---|---|---|---|---|---|---|---|---|---|---|---|---|---|
| | | | 20 | | | | | 25 | | | | | 30 | | |

| Thr | Met | Ser | Trp | Val | Arg | Gln | Thr | Pro | Glu | Lys | Arg | Leu | Glu | Trp | Val |
|---|---|---|---|---|---|---|---|---|---|---|---|---|---|---|---|
| | | 35 | | | | | 40 | | | | | 45 | | | |

| Ala | Thr | Ile | Ser | Ser | Gly | Gly | Gly | Asn | Thr | Tyr | Tyr | Pro | Asp | Ser | Val |
|---|---|---|---|---|---|---|---|---|---|---|---|---|---|---|---|
| | | 50 | | | | 55 | | | | | 60 | | | | |

```
Lys  Gly  Arg  Phe  Thr  Val  Ser  Arg  Asp  Asn  Ala  Met  Ser  Ser  Leu  Tyr
 65                  70                  75                       80

Leu  Gln  Met  Ser  Ser  Leu  Arg  Ser  Glu  Asp  Thr  Ala  Leu  Tyr  Tyr  Cys
                85                  90                       95

Ala  Arg  Tyr  Gly  Ala  Gly  Asp  Ala  Trp  Phe  Ala  Tyr  Trp  Gly  Gln  Gly
               100                 105                      110

Thr  Leu  Val  Thr  Val  Ser  Ala
               115
```

(2) INFORMATION FOR SEQ ID NO:17:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..336

(xi) SEQUENCE DESCRIPTION: SEQ ID NO:17:

```
GAG  CTC  GCG  ATG  ACC  CAG  ACT  CCA  CTC  TCC  CTG  CCT  GTC  AGT  CTT  GGA     48
Glu  Leu  Ala  Met  Thr  Gln  Thr  Pro  Leu  Ser  Leu  Pro  Val  Ser  Leu  Gly
 1                   5                  10                       15

GAT  CAA  GCC  TCC  ATC  TCT  TGC  AGA  TCC  AGT  CAG  AGC  ATT  GTG  CAT  AGT     96
Asp  Gln  Ala  Ser  Ile  Ser  Cys  Arg  Ser  Ser  Gln  Ser  Ile  Val  His  Ser
                20                  25                       30

ACT  GGA  AAC  ACC  TAT  TTA  GAG  TGG  TAC  CTG  CAG  AAA  CCA  GGC  CAG  TCT    144
Thr  Gly  Asn  Thr  Tyr  Leu  Glu  Trp  Tyr  Leu  Gln  Lys  Pro  Gly  Gln  Ser
           35                  40                       45

CCA  AAG  CTC  CTG  ATC  TAC  AAA  GTT  TCC  AAC  CGA  TTT  TCT  GGG  GTC  CCA    192
Pro  Lys  Leu  Leu  Ile  Tyr  Lys  Val  Ser  Asn  Arg  Phe  Ser  Gly  Val  Pro
      50                  55                       60

GAC  AGG  TTC  AGT  GGC  AGT  GGA  TCA  GGG  ACA  GAT  TTC  ACA  CTC  AAG  ATC    240
Asp  Arg  Phe  Ser  Gly  Ser  Gly  Ser  Gly  Thr  Asp  Phe  Thr  Leu  Lys  Ile
 65                  70                  75                       80

AGT  AGA  CTG  GAG  GCT  GAG  GAT  CTG  GGA  GTT  TAT  TAC  TGC  TTT  CAA  GGT    288
Ser  Arg  Leu  Glu  Ala  Glu  Asp  Leu  Gly  Val  Tyr  Tyr  Cys  Phe  Gln  Gly
                85                  90                       95

TCA  CAT  TTT  CCT  CGG  ACG  TTC  GGT  GGA  GGC  ACC  AGG  CTG  GAA  ATC  AAG    336
Ser  His  Phe  Pro  Arg  Thr  Phe  Gly  Gly  Gly  Thr  Arg  Leu  Glu  Ile  Lys
               100                 105                      110
```

(2) INFORMATION FOR SEQ ID NO:18:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:18:

```
Glu  Leu  Ala  Met  Thr  Gln  Thr  Pro  Leu  Ser  Leu  Pro  Val  Ser  Leu  Gly
 1                   5                  10                       15

Asp  Gln  Ala  Ser  Ile  Ser  Cys  Arg  Ser  Ser  Gln  Ser  Ile  Val  His  Ser
                20                  25                       30

Thr  Gly  Asn  Thr  Tyr  Leu  Glu  Trp  Tyr  Leu  Gln  Lys  Pro  Gly  Gln  Ser
           35                  40                       45

Pro  Lys  Leu  Leu  Ile  Tyr  Lys  Val  Ser  Asn  Arg  Phe  Ser  Gly  Val  Pro
      50                  55                       60

Asp  Arg  Phe  Ser  Gly  Ser  Gly  Ser  Gly  Thr  Asp  Phe  Thr  Leu  Lys  Ile
```

-continued

```
              65                      70                        75                         80
Ser  Arg  Leu  Glu  Ala  Glu  Asp  Leu  Gly  Val  Tyr  Tyr  Cys  Phe  Gln  Gly
                        85                   90                            95

Ser  His  Phe  Pro  Arg  Thr  Phe  Gly  Gly  Gly  Thr  Arg  Leu  Glu  Ile  Lys
                   100                  105                       110
```